(12) United States Patent
Fung et al.

(10) Patent No.: US 8,986,278 B2
(45) Date of Patent: Mar. 24, 2015

(54) METHODS AND DEVICES FOR PERICARDIAL ACCESS

(75) Inventors: Gregory W. Fung, San Mateo, CA (US); Russell A. Seiber, Redwood Shores, CA (US); Eduardo A. Sager, Jr., Milpitas, CA (US); Arnold M. Escano, Santa Clara, CA (US); Ryan Douglas Helmuth, Saratoga, CA (US)

(73) Assignee: SentreHEART, Inc., Redwood City, CA (US)

( * ) Notice: Subject to any disclaimer, the term of this patent is extended or adjusted under 35 U.S.C. 154(b) by 554 days.

(21) Appl. No.: 13/086,328

(22) Filed: Apr. 13, 2011

(65) Prior Publication Data

US 2012/0095434 A1 Apr. 19, 2012

Related U.S. Application Data

(60) Provisional application No. 61/323,801, filed on Apr. 13, 2010.

(51) Int. Cl.
*A61M 31/00* (2006.01)
*A61B 17/34* (2006.01)
(Continued)

(52) U.S. Cl.
CPC ......... *A61B 17/3478* (2013.01); *A61B 17/3421* (2013.01); *A61B 17/3415* (2013.01); *A61B 2017/00247* (2013.01);
(Continued)

(58) Field of Classification Search
USPC ........................... 604/500, 528, 272; 606/185
See application file for complete search history.

(56) References Cited

U.S. PATENT DOCUMENTS 3,685,509 A 8/1972 Bentall
4,164,943 A 8/1979 Hill et al.
(Continued)

FOREIGN PATENT DOCUMENTS

CN 102065781 A 5/2011
WO WO-03/066147 A1 8/2003
(Continued)

OTHER PUBLICATIONS

International Search Report mailed on Jul. 1, 2011, for PCT Patent Application No. PCT/US2011/032382, filed on Apr. 13, 2011, 2 pages.
(Continued)

*Primary Examiner* — Kathleen Holwerda
*Assistant Examiner* — Sarah Simpson
(74) *Attorney, Agent, or Firm* — Morrison & Foerster LLP

(57) ABSTRACT

Devices and methods for accessing the pericardial space of a heart are described here. Access devices may generally comprise a tissue-engaging member, a tissue-piercing member, and a guide element. The access device may be introduced to the surface of a pericardium, where the tissue-engaging member may be deployed to engage a portion of the pericardium without engaging the epicardial surface of the heart. Once the access device has engaged the pericardium, the device may manipulate the pericardium to increase the distance between a portion of the pericardium and the epicardial surface of the heart. Once a sufficient space has been created, the tissue-piercing member may be advanced to pierce the pericardium and enter the pericardial space. The guide element may then be introduced into the pericardial space to provide an access pathway to the heart for other devices.

6 Claims, 29 Drawing Sheets

(51) Int. Cl.
 *A61B 17/00* (2006.01)
 *A61B 17/22* (2006.01)
 *A61B 17/32* (2006.01)
 *A61B 18/00* (2006.01)

(52) U.S. Cl.
 CPC ............... *A61B 2017/00309* (2013.01); *A61B 2017/00331* (2013.01); *A61B 2017/00946* (2013.01); *A61B 2017/22038* (2013.01); *A61B 2017/22044* (2013.01); *A61B 2017/320064* (2013.01); *A61B 2017/3488* (2013.01); *A61B 2018/00392* (2013.01)
 USPC ........................................ 604/500; 606/185

(56) References Cited

U.S. PATENT DOCUMENTS

| | | | |
|---|---|---|---|
| 4,222,382 | A | 9/1980 | Antonsson et al. |
| 4,281,659 | A | 8/1981 | Farrar et al. |
| 4,991,578 | A | 2/1991 | Cohen |
| 4,995,866 | A | 2/1991 | Amplatz et al. |
| 5,071,428 | A | 12/1991 | Chin et al. |
| 5,226,890 | A | 7/1993 | Ianniruberto et al. |
| 5,332,398 | A | 7/1994 | Miller et al. |
| 5,407,427 | A | 4/1995 | Zhu et al. |
| 5,695,504 | A | 12/1997 | Gifford, III et al. |
| 5,827,216 | A | 10/1998 | Igo et al. |
| 6,423,051 | B1 | 7/2002 | Kaplan et al. |
| 7,309,328 | B2 | 12/2007 | Kaplan et al. |
| 7,736,347 | B2 | 6/2010 | Kaplan et al. |
| 7,857,822 | B2 * | 12/2010 | Fleischman et al. .......... 606/151 |
| 2004/0167558 | A1 | 8/2004 | Igo et al. |
| 2005/0165466 | A1 | 7/2005 | Morris et al. |
| 2005/0187545 | A1 | 8/2005 | Hooven et al. |
| 2006/0106442 | A1 | 5/2006 | Richardson et al. |
| 2007/0010708 | A1 * | 1/2007 | Ness .............................. 600/115 |
| 2007/0083194 | A1 | 4/2007 | Kunis et al. |
| 2007/0219546 | A1 | 9/2007 | Mody et al. |
| 2008/0294174 | A1 * | 11/2008 | Bardsley et al. ............... 606/108 |
| 2009/0187074 | A1 | 7/2009 | Saadat et al. |
| 2010/0331854 | A1 | 12/2010 | Greenberg et al. |
| 2011/0077672 | A1 * | 3/2011 | Fleischman et al. .......... 606/151 |

FOREIGN PATENT DOCUMENTS

| | | |
|---|---|---|
| WO | WO-2009/120953 A2 | 10/2009 |
| WO | WO-2009/120953 A3 | 10/2009 |

OTHER PUBLICATIONS

Non-Final Office Action mailed on Nov. 22, 2000 for U.S. Appl. No. 09/397,392, filed on Sep. 16, 1999, 3 pages.
Non-Final Office Action mailed on Sep. 21, 2009 for U.S. Appl. No. 11/873,228, filed on Oct. 16, 2007, 8 pages.
Non-Final Office Action mailed on Jul. 9, 2003 for U.S. Appl. No. 10/002,329, filed on Nov. 1, 2001, 7 pages.
Non-Final Office Action mailed on Mar. 22, 2005 for U.S. Appl. No. 10/002,329, filed on Nov. 1, 2001, 7 pages.
Non-Final Office Action mailed on Jun. 29, 2005 for U.S. Appl. No. 10/002,329, filed on Nov. 1, 2001, 7 pages.
Non-Final Office Action mailed on Oct. 3, 2005 for U.S. Appl. No. 10/002,329, filed on Nov. 1, 2001, 8 pages.
Notice of Allowance mailed on Jul. 16, 2001 for U.S. Appl. No. 09/397,392, filed on Sep. 16, 1999, 2 pages.
Notice of Allowance mailed on Jan. 29, 2010 for U.S. Appl. No. 11/873,228, filed on Oct. 16, 2007, 4 pages.
Notice of Allowance mailed on Jan. 28, 2004 for U.S. Appl. No. 10/002,329, filed on Nov. 1, 2001, 4 pages.
Notice of Allowance mailed on Jul. 16, 2007 for U.S. Appl. No. 10/002,329, filed on Nov. 1, 2001, 4 pages.
Restriction Requirement mailed on Aug. 11, 2000 for U.S. Appl. No. 09/397,392, filed on Sep. 16, 1999, 6 pages.
Written Opinion of the International Searching Authority mailed on Jul. 1, 2011, for PCT Patent Application No. PCT/US2011/032382, filed on Apr. 13, 2011, 5 pages.

* cited by examiner

METHODS AND DEVICES FOR PERICARDIAL ACCESS

CROSS-REFERENCE TO RELATED APPLICATIONS

This application claims priority to U.S. Provisional Patent Application Ser. No. 61/323,801, filed on Apr. 13, 2010 and titled "METHODS AND DEVICES FOR PERICARDIAL ACCESS", which is incorporated by reference herein in its entirety.

FIELD

Described here are devices and methods for gaining access to the pericardial space through the pericardium.

BACKGROUND

Access to internal and external structures of the heart may be desirable for the treatment of cardiovascular disease. In some cases, the treatment may involve the delivery of devices to the heart. One way in which a heart may be accessed for device delivery is by an intravascular approach. Intravascular pathways to the heart may involve advancing the device from a femoral vein to the vena cava, through which the chambers and valves of the right side of the heart (e.g., right atrium, right ventricle, etc.) may be accessed. The left side of the heart may also be accessed from this approach by using a transseptal procedure. Alternatively, the left atrium and left ventricle may be intravascularly accessed by a retrograde pathway from the aorta.

However, intravascular access to the heart may not be ideal in all circumstances, such as for the delivery of larger devices, and especially if external structures of the heart are targeted. In such circumstances, the heart may also be accessed through an opening or puncture in the pericardium, which may provide direct access to the external (epicardial) surface of the heart. Accessing the heart via a non-effused pericardium is becoming a recognized access route to the heart. The ability to access the heart via a non-vascular pathway may be useful for a variety of applications, including device or drug delivery, left atrial appendage exclusion, ablation of fibrillating tissue, placement of leads, and the like. Despite these benefits, puncturing the pericardium without contacting and/or damaging the heart itself may prove to be a challenge. Current methods that attempt to reduce this risk involve grasping and/or suctioning the pericardium prior to puncturing it, but the presence of epicardial fat and other irregularities may prevent direct access to the pericardium. In some cases, highly trained physicians may be able to pierce the pericardium without piercing the heart by carefully advancing a needle towards the heart. They may rely on tactile feedback to avoid puncturing the heart, and use this tactile feedback to accommodate and/or compensate for the displacement of the heart and pericardium during a beating heart procedure. However, advancing a needle to the heart by tactile feedback may be particularly risky for inexperienced physicians. Additional methods and devices for accessing the pericardial space are desirable, especially if they are able to provide advantages to existing techniques.

BRIEF SUMMARY

Devices and methods for accessing the pericardial space of a heart are described here. Access devices may generally comprise a tissue-engaging member, a tissue-piercing member, and a guide element. The access device may be introduced to the surface of a pericardium, where the tissue-engaging member may be deployed to engage a portion of the pericardium without engaging the epicardial surface of the heart. Once the access device has engaged the pericardium, the device may manipulate the pericardium to increase the distance between a portion of the pericardium and the epicardial surface of the heart. Once a sufficient space has been created, the tissue-piercing member may be advanced to pierce the pericardium and enter the pericardial space. The guide element may then be introduced into the pericardial space to provide an access pathway to the heart for other devices.

In one variation, a device for accessing the pericardial space may comprise a tissue-piercing member having a first longitudinal lumen and a second longitudinal lumen, a tissue-engaging member that may be advanced through the first longitudinal lumen, a first guide element that may be advanced through the second longitudinal lumen, and a handle actuator. The first and/or second longitudinal lumens may be configured to pass a fluid and/or a guide element therethrough. The actuator may be configured to actuate the tissue-piercing member, the tissue-engaging member, and the first guide element. In some variations, the tissue-piercing member may have a sharpened and/or beveled distal tip. The tissue-piercing member may also have a tapered distal tip. Variations of tissue-piercing members may include components that mechanically cut or pierce tissue, e.g., a needle, a lancet, a blade, etc., components that chemically etch tissue, e.g., enzymes, acids, components that electrically weaken tissue, e.g., electrical probes, and/or components that thermally weaken tissue, e.g., cryo probes and cryogenic substances.

Various tissue-engaging members may be advanced through the first lumen of the needle. The surface of the tissue-engaging members may be modified to increase the coefficient of friction, for example, the surface may be textured or coated. In some variations, the coating may be hydrophilic, hydrophobic, and/or may be or include an adhesive. Tissue-engaging members may have any shape suitable for engaging and manipulating the pericardium, for example, at least a part of the distal end of the tissue-engaging member may be in the form of a corkscrew or sawtooth. In some variations, tissue-engaging member may comprise one or more tissue-engaging elements, where the tissue-engaging elements may have a first undeployed configuration, where the tissue-engaging elements are compressed in the first lumen, and a second deployed configuration, where the tissue-engaging elements are expanded.

Certain variations of a tissue-piercing member may comprise one or more side openings at a position proximal to the distal end of the tissue-piercing member, where the one or more side openings are in communication with the first lumen. The side openings may be sized and shaped for the passage of one or more tissue-engaging members and/or tissue-engaging elements.

A variety of tissue-engaging elements may be used with a tissue-engaging member. For example, at least a part of the distal end of the tissue-engaging elements may be in the form of tines, hooks, grapnels, antennae with tissue-grasping structures, and/or teeth, and may additionally have one or more modifications on their surface to increase the coefficient of friction.

In some variations of a device for accessing the pericardial space, the first guide element is a guide wire. The device may also comprise a second guide element, and both the first and second guide elements may be guide wires.

Also described here is one variation of a system for accessing the pericardial space of a heart. This variation comprises an access device having a tissue-piercing member, a tissue-engaging member, and a first guide element, where the tissue-engaging member and first guide element are housed in the tissue-piercing member. The system may also comprise a sheath and a carbon dioxide insufflation device that is configured to attach to the access device. Optionally, the system may also comprise a second guide element.

Methods of accessing the pericardial space of a heart are also provided. One variation of a method of accessing the pericardial space of the heart comprises introducing an access device in the proximity of the surface of the pericardium, where the access device may comprise a tissue-piercing member, one or more tissue-engaging members, and a guide element, where the tissue-engaging members and guide element may be housed in the piercing member, deploying the tissue-engaging members, engaging a portion of the pericardium, manipulating the portion of the pericardium to increase the distance between a portion of the pericardium and the heart, advancing the tissue-piercing member into the pericardial space, and advancing the guide element into the pericardial space. The access device may be introduced percutaneously or minimally invasively. Optionally, the method may also comprise confirming that the tissue-piercing member has entered the pericardial space before advancing the guide element. The guide element may be advanced mechanically, and/or machine-controlled, where the machine may advance the guide element according to a pre-programmed sequence or according to user input. The guide element may be advanced manually by the user. In some variations of the method, manipulating the pericardium may comprise twisting or rotating the pericardium, which may separate the pericardium from the heart. Additionally or alternatively, manipulating the portion of the pericardium may comprise advancing the tissue-engaging members to engage the pericardium, retracting the tissue-engaging members to increase the distance between a portion of the pericardium and the heart, and advancing the tissue-piercing member to enter the pericardial space. In some variations, the heart and surrounding pericardial structures may be imaged throughout the procedure.

BRIEF DESCRIPTION OF THE DRAWINGS

FIGS. 5A-5F illustrate another variation of an access device that may be used with the variation of the method depicted in FIG. 4A.

FIGS. 10A-10G depict the use of an access device to engage, manipulate, and penetrate the pericardium of a heart to access the pericardial space.

DETAILED DESCRIPTION

Figure 1:
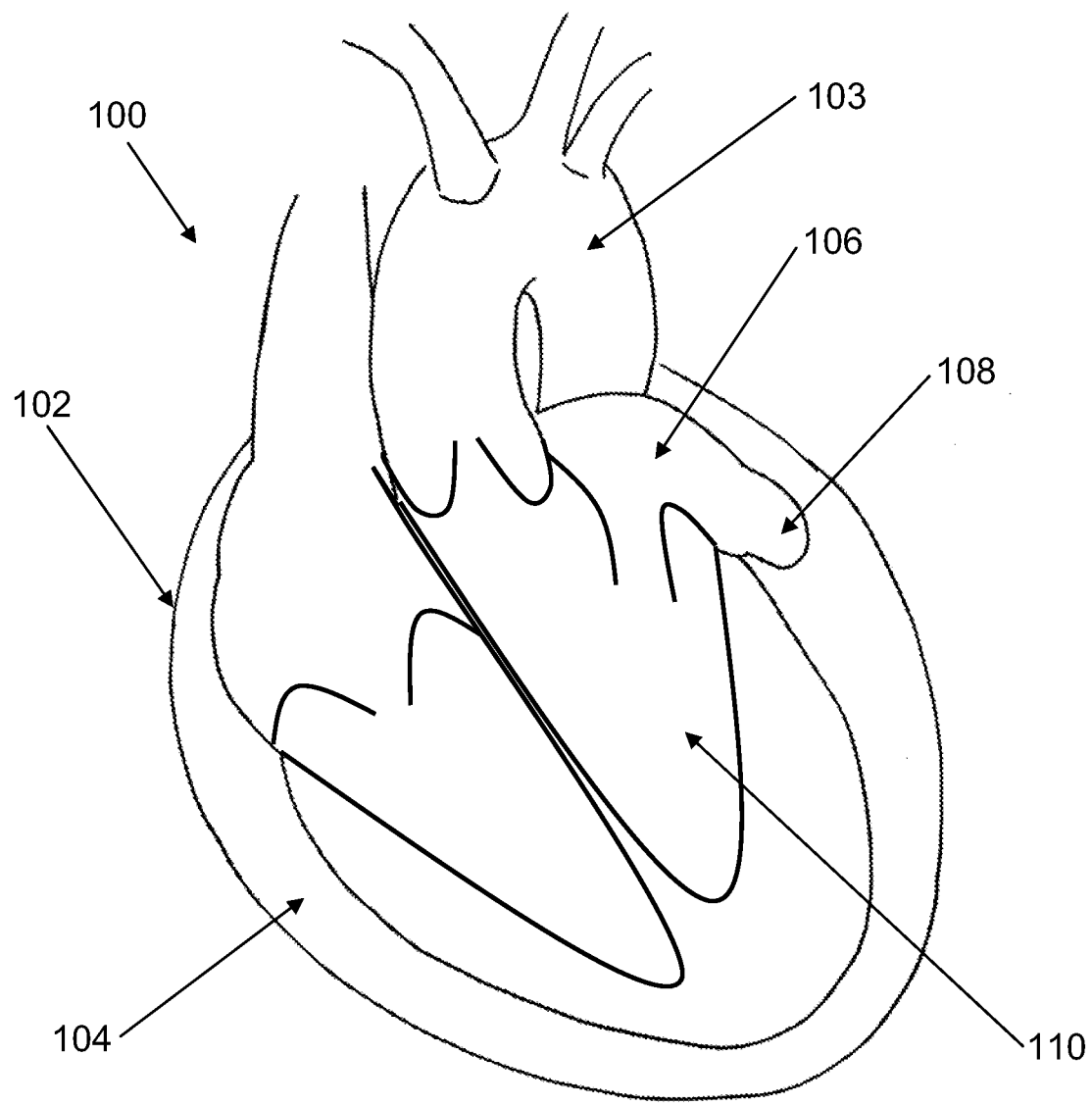
FIG. 1 depicts a cross-section of a heart.

The devices and methods described here may be used to access the heart and the pericardial space through a puncture in the pericardium. FIG. 1 depicts a heart (100) enclosed by a pericardium (102). FIG. 1 also depicts various anatomical structures of the heart, including the left atrium (106), left atrial appendage (108), left ventricle (110), and the aortic arch (103). The pericardium (102) is filled with a fluid that may separate it from the heart. The space between the pericardium (102) and heart (100) is the pericardial space (104). The distance between the pericardium and the surface of the heart may vary. For example, the pericardium may be about 5 millimeters away from heart in some areas, while the pericardium may directly contact the heart (100) in other areas. As such, it may be difficult to puncture the pericardium (102) without contacting, puncturing and/or damaging the heart's surface (100). The devices and methods described below may be used to increase the distance between a portion of the pericardium and the heart at the intended pericardial puncture site to minimize the risk of damaging the heart.

While the devices and methods described here are described in reference to puncturing the pericardium to provide access to the heart, it should be understood that these devices and methods may be used to create a puncture in or otherwise facilitate access to any fluid-filled membrane or sac to access the structures therein, e.g., dura mater, peritoneum, amniotic sac, etc.

I. Access Devices

Various devices may be used to puncture the pericardium in order to access the pericardial space. Typically, these access devices are configured to engage and manipulate the pericardium, puncture it, and advance a guide element into the pericardial space. In some instances, engaging and manipulating the pericardium may involve grasping the pericardium to separate it from the surface of the heart to form an enlarged, tent-like, region of the pericardial space. The enlarged region of the pericardial space may serve as a buffer between a piercing member of the access device and the surface of the heart, which may help reduce the risk of inadvertent puncture or damage to the heart. Once access to the pericardial space has been achieved, a portion of one or more guide elements may then be placed into the pericardial space, and may provide an access route to the pericardial space. This access to the pericardial space may allow for one or more procedures to be performed in, around, or through the pericardial space, as will be described in more detail below. The access devices generally comprise one or more components that may achieve one or more of the engaging, manipulating, puncturing, and advancing steps. For example, the access devices described here may comprise one or more sheaths, one or more tissue-engagement members, one or more tissue-piercing members, and one or more guide elements. These devices may be configured for percutaneous or minimally invasive approaches to the heart. For example, the device components may be sized and shaped to allow a practitioner to atraumatically advance the device towards the pericardium.

Figure 2A:
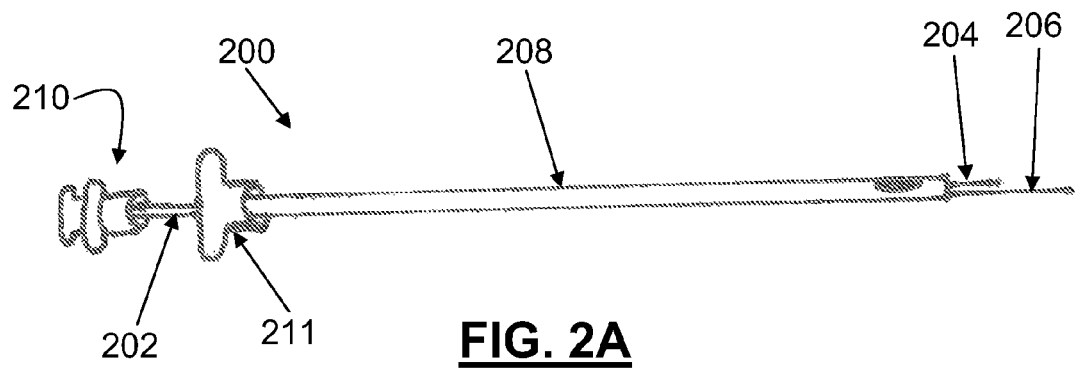
FIG. 2A depicts one variation of an access device that may be used to access a pericardial space of the heart.

One variation of a device for accessing the pericardial space is shown in FIGS. 2A-2E. FIG. 2A depicts access device (200) which comprises a tissue-piercing member (202), a first guide element (204), a second guide element (206), a sheath (208), a tissue-piercing member actuator (210), a sheath actuator (211), and a tissue-engaging member (not shown). Generally, sheath (208) may help aid in advancement of various components of device (200) to a position near the pericardium. Once in place, the tissue-engaging member may engage and/or manipulate the pericardium and the tissue-piercing member (202) may pierce, puncture, or otherwise penetrate the pericardium. One or more guide elements (e.g., first guide element (204) and/or second guide element (206)) may then be placed through the pericardium into the pericardial space, and may provide an access route for other devices into the pericardial space. Each of these components is described in more detail below, as are methods of using the access devices described here.

Figure 2B:
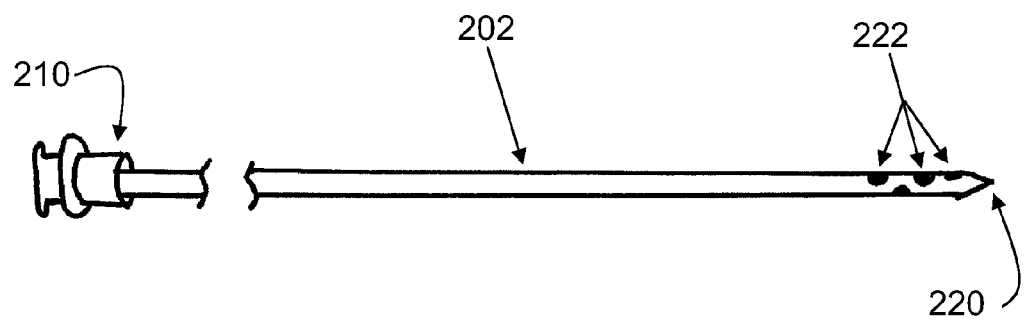
FIGS. 2B-2D depict the individual components of the access device of FIG. 2A.

As mentioned above, the access devices described here may comprise a tissue-piercing member for piercing, puncturing, or otherwise facilitating access through the pericardium. FIG. 2B depicts one variation of a tissue-piercing member (202) that may be used with the access device (200) described immediately above. As shown there, the tissue-piercing member (202) comprises a body (201) having a tissue-piercing distal tip (220), a plurality of side apertures (222), and one or more working longitudinal lumens (not shown) extending at least partially therethrough. The tissue-piercing member may be a needle or other elongate member with a sharpened distal tip, similar to what is shown here. For example, in some variations, the body and the tissue-piercing distal tip (220) may be formed from a single piece of material. In other variations, the tissue-piercing distal tip may be formed separately from the body and may be attached thereto. For example, in some instances, it may be desirable to make the body of the tissue-piercing member from a flexible material (e.g., one or more metal braids, a shape memory alloy, or the like), but make the tissue-piercing distal tip from a rigid metal or other material. In these instances, the flexible body may allow for easier manipulation or maneuvering of the tissue-piercing member through the anatomy, while the rigid distal tip may be sufficiently hard to puncture tissue.

The tissue-piercing members used here may pierce, puncture or otherwise pass through tissue above. For example, as described above, in some variations, the tissue-piercing member may comprise a sharpened edge or tip, or tissue-piercing distal tip (220) that is beveled or tapered. In other variations, the tissue-piercing member distal tip may comprise a cutting element that may form a slit in the pericardium, for example, a single blade, or two or more blades joined by a pin that allows the blades to open and close. In still other variations, the tissue-piercing member distal tip may comprise a port for chemical agents that may create an opening in the pericardium, for example, enzymes or acids that may etch through a portion of the pericardium.

In still other variations, a tissue-piercing member may create an opening in the pericardium (or otherwise weaken tissue of the pericardium) by ablating tissue by applying a current. The tissue-piercing member may be configured to ablate tissue in any suitable member. In some variations, one or more electrodes may be passed through the body of the tissue-piercing member and through a port or apertures in the body of the tissue-piercing member, (e.g., through one of side apertures (222) of tissue-piercing member (202) described above). In other variations, one or more portions of the tissue-piercing member may be configured to deliver energy to tissue (e.g., may be made at least partially from an electrically conductive tissue-piercing member). The tissue-piercing members (or electrodes inserted therethrough) may apply current pulses, for example, 10 pA to 1000 pA, or may apply a certain current density to thin out a region of the pericardium. Alternatively or additionally, tissue-piercing members may be arranged to create a potential drop (i.e., voltage) between the internal and the external side of the pericardium, for example, 10 mV to 500 mV, which may weaken a portion of the pericardium. Tissue-piercing members may also create an opening in the pericardium (or otherwise weaken the pericardium) by applying focal bursts of positive pressure to the pericardium via the tissue-piercing member. Tissue-piercing members may also create an opening in the pericardium by freezing a portion of the pericardium, e.g., using cryocautery and/or cryosurgical instruments and techniques. Some tissue-piercing members may employ a combination of the above methods (e.g., physical cutting and electrical ablation, chemical etch with electrical ablation, electrical ablation with pressure pulses, chemical etch with pressure pulses, etc.) to create an opening in or otherwise weaken the pericardium.

As shown in FIG. 2B, tissue-piercing member (202) may comprise one or more side apertures (222). It should be appreciated that while the tissue-piercing members described here may comprise a single side aperture or a plurality of side apertures (e.g., 2, 4, 6, 12, 25, etc.), other variations of the tissue-piercing members may not comprise any side apertures. In variations that do comprise side apertures, such as side apertures (222) shown in FIG. 2B, the side apertures may be in communication with one or more of the working lumens of the tissue-piercing member, such that one or more devices or substances may be passed therethrough. For example, in some variations, one or more side apertures of the tissue-piercing member may be sized and configured such that one or more guide elements (e.g., a guide wire or catheter) may pass therethrough to exit the tissue-piercing member. In other variations, one or more substances (e.g., contrast solutions) passed into a working lumen of the tissue-piercing member may exit the tissue-piercing member through one or more of the side apertures.

Additionally, as mentioned above, the tissue-piercing member may comprise one or more longitudinal working lumens extending at least partially through the body of the tissue-piercing member. It should be appreciated that the tissue-piercing members described here may comprise a single working lumen or a plurality of working lumens (e.g., two, three, or four or more), or in some instances may not comprise any working lumens. The working lumens may be configured to slidably house one or more of a variety of devices, for example, tissue-engaging devices, guide elements, and the like. Tissue-piercing member (202) may be forged or otherwise formed from a tube, e.g., a hypotube, made of any inert, biocompatible material, for example, metallic materials such as stainless steel, nickel titanium alloy, and/or polymeric materials such as Teflon®, polyethylene, polypropylene, polyetheretherketone (PEEK), etc. Tissue-piercing member (202) may be a single continuous tube, or may be a series of articulated segments. As mentioned above, in other variations, the tissue-piercing member may not have a longitudinal lumen at least partially therethrough, and may be, for example, a lancet, scalpel, or wire. In some variations, a steerable tissue-piercing member may be made of a single, flexible material, or may comprise two or more articulated segments that may be joined by hinges. Certain variations of the tissue-piercing member may have one or more pre-shaped curves, where the pre-shaped curves may be flexible or rigid, as appropriate.

The working lumens associated with the tissue piercing member (as well as any longitudinal lumens associated with tissue-engaging members, devices, and/or tubular bodies as described hereinthroughout) may be formed by any suitable method. For example, the tissue-piercing member may be made from a tube, e.g., a hypotube, or any suitable tubular structure, where the one or more longitudinal lumens therethrough is formed in the course of manufacturing the tube. Alternatively or additionally, a tube with a diameter smaller than a tissue-piercing member with a first lumen may be inserted through the first lumen, and the tube may be welded, bonded, or otherwise attached to an inner surface of the tissue-piercing member lumen to form a second needle lumen. In other variations, the tissue-piercing member may be formed from two or more small diameter tubes that are welded or bonded together, and additionally one of the tubes may possess a sharpened distal tip. The tubes may be nested one inside the other, or may be arranged side-by-side, i.e., the two or more tubes may have longitudinal axes that are parallel to each other. Certain longitudinal lumens may be concentric with the tissue-piercing member. In other variations, the longitudinal lumens may be located on the outer circumference of the tissue-piercing member, and may themselves be tubes welded, bonded, or stamped to the external surface of the needle. While some variations of a tissue-piercing member may have longitudinal lumens that have a closed-shape (e.g., a circle, rectangle, hexagon, octagon, and the like), other longitudinal lumens may have one or more side slots or apertures. In some variations, the longitudinal lumen may have a partially-open geometry, e.g., have a C-shaped cross-section, or may have a longitudinal side aperture that extends at least a longitudinal portion of the lumen. Any number or configuration of longitudinal lumens may be associated with tissue-piercing members (and other device components) as needed for accessing the pericardial space.

The movement of the tissue-piercing member (202) may be controlled by the tissue-piercing member actuator (210), which is positioned at the proximal end of the tissue-piercing member (202). A tissue-piercing member actuator may be any structure (e.g., a handle) configured to move and steer the tissue-piercing member along one or more degrees of freedom. For example, the tissue-piercing member (202) may be advanced along one axis, e.g., forward and backward along a longitudinal axis, or may be steered along multiple axes and planes, e.g., rotated around a longitudinal axis, flexed or bent transversely to the longitudinal axis, etc. In some variations where the tissue-piercing member has one or more pre-shaped curves in one or more planes, the tissue-piercing member actuator may move along one axis, but the tissue-piercing member may pierce along a different axis. The tissue-piercing member actuator (210) may also be configured to advance the tissue-piercing member (202) towards a tissue target, and to retract the tissue-piercing member away from the tissue target. In variations where the tissue-piercing member is steerable or otherwise configured to change shape, the actuator may comprise one or more controls for steering or maneuvering the tissue-piercing member. In some variations, the tissue-piercing member actuator may be computer-controlled or otherwise robotically controlled, where the tissue-piercing member may be moved according to a pre-programmed sequence, or the tissue-piercing member actuator may be manually controlled by the practitioner. Additionally, in variations where one or more guide elements, substances, or other devices are advanced through a working lumen of the tissue-piercing member, the tissue-piercing member actuator may comprise one or more ports, valves, or other structures for introducing the guide elements, substances, or other devices into the working lumen.

Figure 2C:
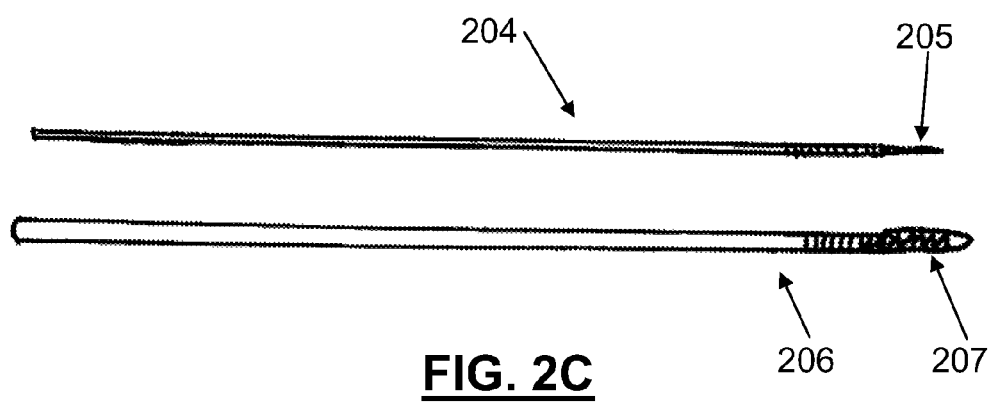

The access devices described here may comprise one or more guide elements that may be at least partially placed through the pericardium into the pericardial space. Once placed in the pericardial space, the guide elements may provide an access route along which one or more devices may pass to enter the pericardial space, as will be described in more detail below. FIG. 2C illustrates two variations of guide elements suitable for use with access device (200), specifically small guide wire (204) and large guide wire (206), each which may be passed through either the tissue-piercing member (202) or the sheath (208). The choice of guide element may be determined, in part, by the devices that may be advanced along or through the. The small guide wire (204) may have a diameter of about 0.014 inch to about 0.030 inch, for example 0.025 inch, while the large guide wire (206) may have a diameter of about 0.025 inch to about 0.038 inch, for example, 0.035 inch. In some variations, the guide wires (204) and (206) may each have a longitudinal lumen (not shown) at least a portion therethrough for passing other devices, for instance, other guide elements and/or sutures. For example, a large guide wire (206) may have a lumen that is sized for passing the small guide wire (204) therethrough. Furthermore, guide elements may have a smooth, low-friction surface with may facilitate device delivery. The distal ends (205) and (207) of guide wires (204, 206) may be slotted or segmented, which may provide additional flexibility and aid advancement and maneuverability of the guide wires (204) and (206). Guide wires (204) and (206) may be made of any inert, biocompatible material, for example, nickel titanium alloy, stainless steel, or polymeric materials such as polyethylene, nylon, polypropylene, PVC, and the like. In some variations, the distal ends (205, 207) may be rounded or otherwise atraumatic, while in other variations, they may be capable of piercing tissue, as may be desirable depending on the characteristics of the pericardium (e.g., thickness, amount of fat deposition, movement due to the beating heart, etc.). The distal end (205) may be atraumatic, while the distal end (207) may be sharp, and vice versa. The movement and navigation of the guide wires (204, 206) may be actuated by a proximal handle actuator. For example, in some variations a tissue-piercing member actuator (210) may comprise one or more controls or other structures for advancing or otherwise maneuvering one or more guide wires. While shown in FIGS. 2A-2D as having two guide wires (small guide wire (204) and large guide wire (206)), the access devices described here may comprise any number of guide elements (e.g., one, two, three or more) and may include any suitable guide element or combination of guide elements (e.g., one or more guide wires, one or more catheters, or the like).

Figure 2D:
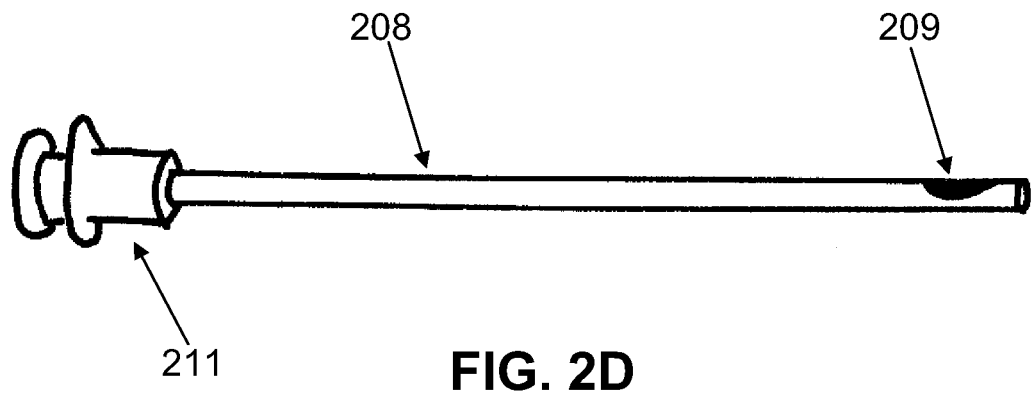

As mentioned above, one or more portions of the access devices described here (e.g., guide wires (204) and (206) and/or tissue-piercing member (202) of access device 200 described in more detail above) may optionally be at least partially housed and/or advanced through a sheath. For example, as shown in FIG. 2D, access device (200) may comprise a sheath (208). As shown there, sheath (208) comprises a sheath actuator (211), a longitudinal lumen (not shown) and a side opening (209). The sheath actuator (211) may be configured to control, steer, or otherwise maneuver the sheath (208) through the anatomy, and may comprise one or more apertures, ports, and/or valves (not shown) through which one or more devices or device components may be advanced. The sheathes described here may comprise any suitable number of longitudinal lumens (e.g., one, two, three, or four or more longitudinal lumens), and these lumens may be formed in any suitable manner, such as those described above. The longitudinal lumen or lumens may be configured for the passage of one or more portions of the access device (e.g., one or more guide elements, one or more catheters, one or more tissue-engaging members, one or more tissue-piercing members, combinations thereof and the like) one or more therethrough. In some variations, each of the access device components may pass through a single lumen of the sheath (208). In other variations, the sheath (208) may comprise first and second lumens, where the first lumen may be configured to slidably house the tissue-piercing member and tissue-engaging elements, and a second lumen may be configured to house one or more guide elements (e.g., the first (204) and/or second (206) guide element). In variations where one or more devices are advanced along or through a guide element placed at least partially within the pericardial space, these devices may be advanced through the sheath, as will be described in more detail below. Additionally or alternatively, one or more fluids or substances (e.g., contrast solution) may be passed through the sheath. It should also be appreciated that while shown in FIGS. 2A-2D as being controlled by separate actuators (tissue-piercing member actuator (210) and sheath actuator (211)) the sheath (208) and tissue-piercing member (202) may be controlled by a single handle or actuator. Indeed, the access devices described here may be configured to comprise a plurality of handles for controlling various components of the access device, or may comprise a single handle which controls each of the device components.

As shown in FIG. 2D, sheath (208) may comprise a side opening (209), but need not comprise a side opening. In variations that do include a side opening, the sheath may comprise any suitable number of side openings (e.g., one, two, three, or four or more). Side opening (209) may be sized and shaped for the passage of therapeutic agents, contrast agents, or the like therethrough, as well as for the passage of devices that may be advanced through the longitudinal lumen. Side opening (209) may be located towards the distal end of the sheath (208), as shown in FIG. 2D, but may be in any suitable location, for example, a location such that it is generally aligned and in communication with the side apertures (222) of the tissue-piercing member (202). In some variations, there may be a plurality of side openings, for example, there may be equal numbers of side apertures (222) and side openings (209).

In some variations, the sheath (208) may also be steerable. A steerable sheath may be formed of a single tube made of a flexible material, or may have multiple articulating segments, where each segment is connected by a hinge. Alternatively or additionally, a sheath may have one or more pre-shaped curves. For example, a sheath and a tissue-piercing member may have the same number of pre-shaped curves that match each other, and/or may both be steerable with the same degrees of freedom. In other variations, a sheath and a tissue-piercing member may have different degrees of freedom, for example, the sheath may be stationary while the tissue-piercing member may be steerable, or vice versa. A sheath (208) may be made of any inert, biocompatible material that provides the desired amount of structural support and maneuverability, for example, certain metallic materials such as stainless steel and/or any polymeric materials such as polyethylene, nylon, polypropylene, PVC and the like. In some variations, sheath (208) may have a diameter that may help to reduce trauma to surrounding structure, for example, the diameter of sheath (208) may range from 0.053 inch to 0.210 inch. Sheath (208) may be forged from a stainless steel tube, e.g., a hypotube, or extruded using a metallic or polymeric substrate.

In certain variations of an access device, guide wire(s), catheter(s), and tissue-engaging members may be advanced through a cannula or other guide element as suitable for the access route selected (e.g., from a right or left intercostal site, a sub-thoracic site, below the diaphragm, and the like). Alternatively or additionally, the access device may comprise multiple sheaths or tubes with tapered shapes that may be slidably nested. As each nested sheath is advanced distally outward, the distal portion of the access device may be urged towards the pericardium. Some variations of access device may also comprise one or more dilators.

Figure 9A:
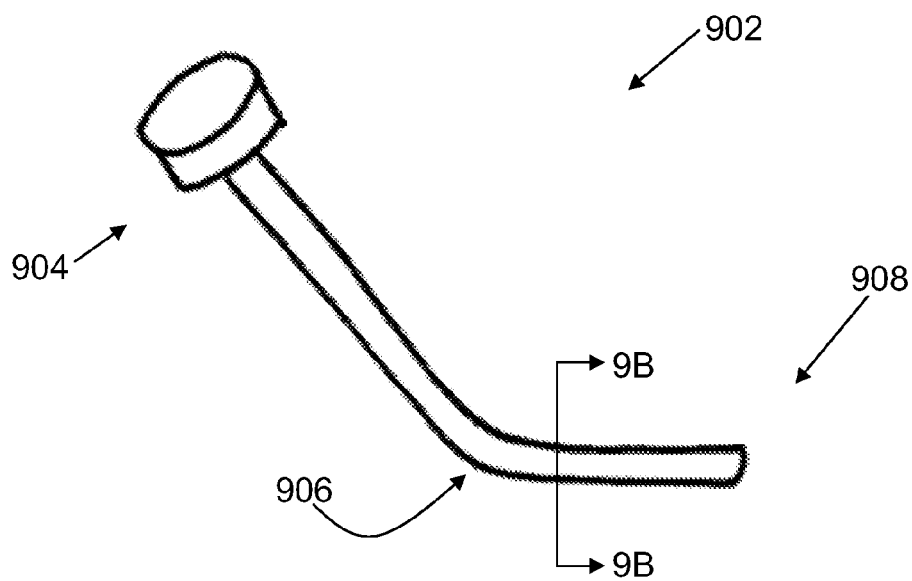
FIGS. 9A-9D depict a variation of a sheath that may be used with the devices and methods described here to access the pericardial space of a heart.
Figure 9B:
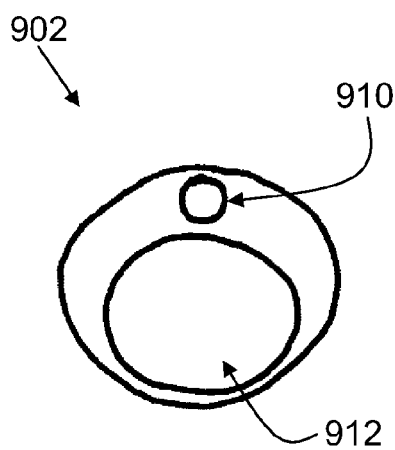

As mentioned above, the sheaths of the access devices described here may comprise one of more curves for facilitating access to the heart. In these variations, additional components of the access device (e.g., needle, guide elements, tissue-piercing elements, etc.) may be sized and shaped to correspond with the one or more curves in the sheath. One example of a sheath with one or more curves is shown in FIGS. 9A and 9B. As shown there, the sheath (902) may have a curved region (906) between the proximal portion (904) to the distal portion (908). The proximal portion (904) may be connected to a sheath actuator, as previously described. A sheath actuator may be used to advance the sheath, e.g., along a longitudinal axis, to navigate the distal portion of the sheath, and/or may be configured to cause the curved region (906) to bend. The curved region (906) may have one or more pre-shaped curves, or may be flexible or bendable using a suitable actuating mechanism controlled by the sheath actuator at the proximal portion (904). A cross-section of the sheath (902) is depicted in FIG. 9B. The sheath (902) may have one or more longitudinal lumens therethrough, for example, a wire lumen (910) and an access device lumen (912). The wire lumen (910) may be sized and shaped for passing a wire therethrough. Adjusting the tension on the wire may alter the curvature of the curved region (906). For example, increasing the wire tension may cause bending of the curved region (906), while decreasing the wire tension may cause straightening of the curved region (906). Other variations of a curved or bendable sheath may have any desired number of lumens therethrough, e.g. 2, 3, 5, 8, etc. The access lumen (912) may be sized and shaped to pass a pericardial access device therethrough, for example, any of the access devices described above. In some variations, sheaths may have additional lumens for inserting other devices therethrough, and/or as necessary for accommodating mechanisms that may be used to control the flexion of the curved region (906).

Figure 9C:
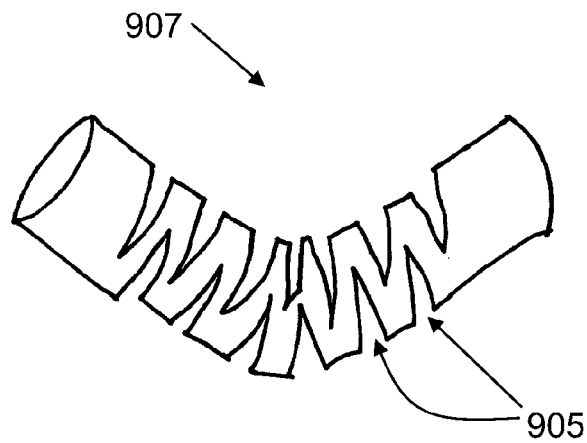

The curved region (906) may be made of a flexible or bendable material, or may be made of a substantially rigid material arranged in articulating segments that allow for the curved region (906) to bend when actuated. The curved region (906) may be integrally formed with the body of the sheath (902), or may be separately formed and attached to the sheath (902). For example, the curved region (906) may be made of polymeric tubing and/or materials such as Pebax®, nylon, fluoropolymers (e.g., PTFE, FEP), polyethelene, Teflon®, polyethylene terephthalate (PET), Tecothane®, etc. In some variations, the curved region (906) may be made of a polymeric tube with reinforced stainless steel or nitinol. Where the curved region (906) is made of a substantially rigid material, for example, stainless steel, nickel titanium, nitinol, cobalt alloys (e.g. nickel-cobalt, cobalt-nickel-chromium-molybdenum), and/or polymers such as PEEK, polyethylene (HDPE), polyimide, etc., the curved region may be slotted or segmented to allow bending to occur. In some variations, a curved region (907) may have one or more slots (905), as illustrated in FIG. 9C. In other variations, the curved region (906) may comprise a plurality of segments, where the positioning of the segments with respect to each other is controlled by a wire or pivot mandrel. The segments may be coupled together via mechanical hinges and/or living hinges. Sheaths may also comprise multiple curved regions, where each of the curved regions may have the same or different radii of curvature. For example, one curved region may be made of a material with a certain flexibility, while another curved region may be made of a material with a different flexibility. Other curved regions may be slotted or segmented, as appropriate. Different curved regions may be separated by a straight portion of the sheath, or may be contiguous. A plurality of curved regions may help to provide additional maneuverability to navigate the distal portion of the sheath to the targeted region of the heart.

In some variations, the curvature of the curved region (906) may be locked or fixed, e.g., the curved region (906) is first actuated to attain a desired degree of curvature, then locked to retain that desired curvature. Suitable locking mechanisms may include, for example, maintaining the tension of a wire that may be inserted through the wire lumen (910), or immobilizing the hinge mechanisms to a desired configuration. A flexible or soft curved region may be locked into position by fixing the configuration (e.g., curvature, tension, etc.) of the wire within the wire lumen (910). Some variations of a sheath may have a pre-shaped curve, where the radius of curvature is determined at the time of manufacture, and remains unchanged as the sheath is used.

As mentioned previously, any of the pericardial access devices above may be used with a sheath that has one or more curved regions. The needles, tissue-piercing members, guide elements of the access devices may have features that allow them to move through a curve in the sheath. For example, the needles, tissue-piercing members, and guide elements of the access devices may be bendable, flexible, slotted (similar to the slots depicted in FIG. 9C), pliable, and/or may have hinged regions (mechanical or living), pre-shaped curves and the like, such that they are configured to pass through any curves in the sheath. In some variations, the access devices may have pre-shaped curves that match the curves in the sheath.

Figure 9D:
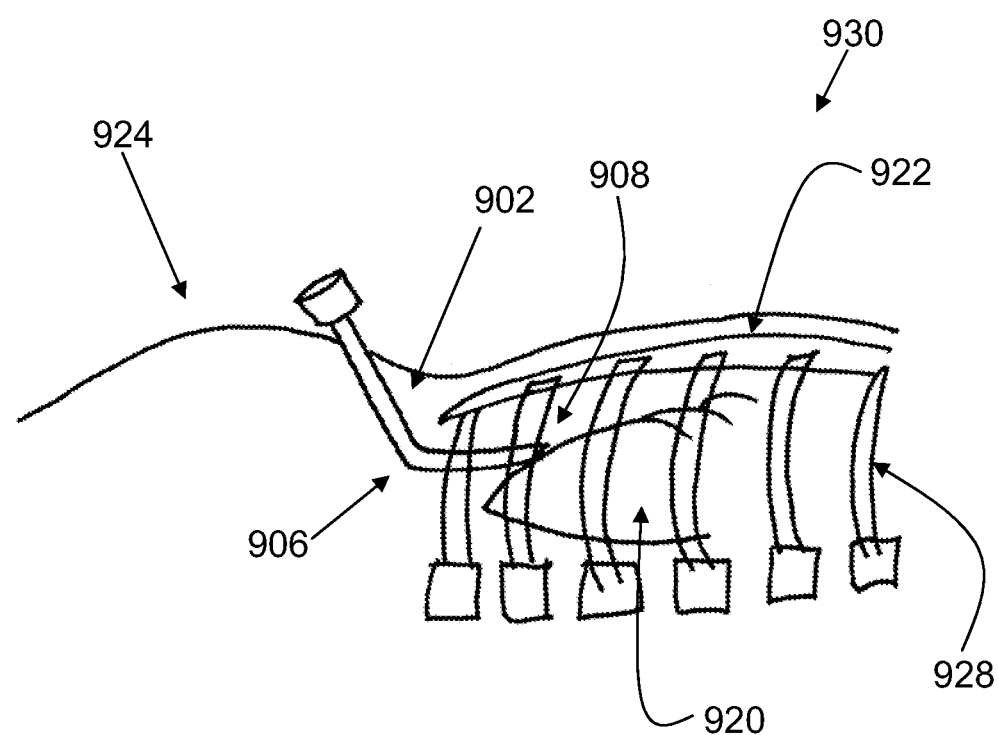

FIG. 9D depicts one variation of a method of using the sheath (902). The sheath (902) may be inserted into the subject (930) at a location beneath the sternum (922). Prior to insertion, the sheath may be substantially straight, or may be curved, as appropriate. Once the sheath (902) has been inserted, the curved region (906) may be adjusted in order to bring the distal portion (908) close to the surface of the heart (920). For example, the distal portion (908) may be navigated underneath the ribs (928) towards the heart (920). Once the distal portion (908) of the sheath (902) is in a desired location, e.g., an anterior and/or slightly lateral side of the heart, the curved region (906) may be locked to retain the curvature of the curved region. The location of the distal portion (908) may be monitored using any suitable imaging modality, for example, ultrasound, fluoroscopy, and the like. In some methods, the location of the distal portion (908) may be monitored by tactile feedback.

An articulating sheath such as is shown and described above, may be useful for accessing the heart (920) where the abdomen (924) of the subject (930) may limit the angle at which the sheath (902) may be positioned. Certain subject anatomy, such as a smaller abdomen (924) may provide a large range of maneuverability for the sheath (902), while a larger abdomen (924) may limit the range of maneuverability for the sheath. Providing one or more curved regions may allow the heart to be more readily accessed where subject anatomy limits the range in which the sheath may be positioned. For example, providing one or more curved regions may help to reduce the force that may be required to position the sheath (902), and may provide additional access paths to the heart in the event the originally planned pathway becomes unavailable.

While some of the access devices described here may comprise a sheath, other access devices may not have a sheath and sheath actuator. Indeed, in some variations, one or more portions of the access device may be advanced without the aid of sheath. For example, in some variations, an access device may comprise a tissue-piercing member, such as those described in more detail above, which may be advanced without a sheath. Such a tissue-piercing member may have one or more longitudinal lumens at least partially therethrough, as well as one or more side apertures. In some of these variations, one or more components of the access device (e.g., one or more guide elements, one or more catheters, one or more tissue-engaging members, combinations thereof, and the like) may be advanced through one or more lumens of the tissue-piercing member. Additionally or alternatively, one or more components of the access devices may be advanced separately from the tissue-piercing member.

Figure 2E:
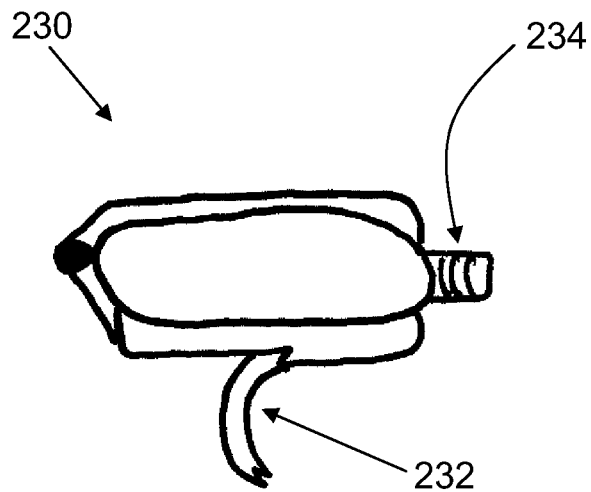
FIG. 2E depicts a variation of an insufflator which may be used with the access device of FIG. 2A.

Optionally, an access device (e.g., access device (200)) may further comprise a gas or liquid fluid source that may be connected to one of the lumens in a tissue-piercing member (e.g., tissue-piercing member (202)) and/or a sheath (e.g., sheath (208)). Insufflating the pericardium using a gaseous and/or liquid compound may help to increase the distance between a portion of the pericardium and the heart. This may enable the pericardium to be pierced without piercing the heart. As shown in FIG. 2E, a carbon dioxide insufflator (230) may be included with an access device (200), however, it should be understood that other types of gases or fluids may also be used including but not limited to carbon dioxide ($CO_2$), nitrous oxide ($N_2O$), helium (He), air, nitrogen ($N_2$), argon (Ar) or fluorinated gases such as dodecafluoropentane, octafluoropropane, decafluorobutane, saline, anti-inflammatory agents such as hyaluronic acid, triamcinolone, etc. A carbon dioxide insufflator (230) may comprise a flow regulator (232) and a valve (234). A flow regulator (232) may be manually or machine-adjusted to provide the quantity of gas that is needed to prepare the pericardial space for puncture. In some variations, the flow regulator may regulate the flow of the gas according to a pre-programmed algorithm, and/or may be adjusted in response to real-time measurements (e.g., imaging, sensor, and/or physiological data). The valve (234) may be sized and shaped to interlock with the actuators (210) and/or (211), for example, the interlock may be a Luer-Lok™, Luer-Slip™, a friction-fit, snap-fit, screw-fit, or any suitable connector mechanism. The valve (234) may be actuated concurrently with the other actuators on the access device (200), or may be actuated independently. The valve may be actuated in conjunction with the tissue-piercing member and/or the sheath, or may be independently actuated. In some variations, the tissue-piercing member and the sheath may be actuated together, while in other variations, they may be actuated independently.

Figure 3A:
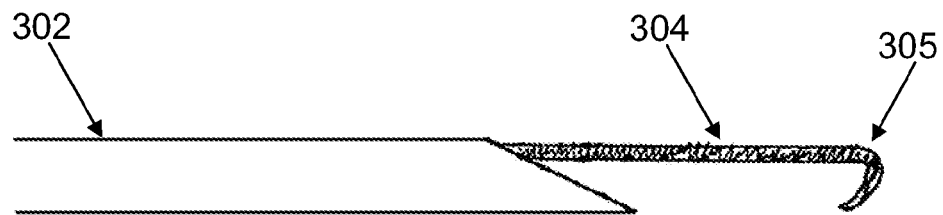
FIGS. 3A-3H depict variations of a tissue-engaging member that may be used with an access device to engage and manipulate the pericardium of a heart.

As described above, the access device (200) may comprises one or more tissue-engaging members. Generally, the tissue-engaging members may engage a portion of the pericardium, which may allow for manipulation of the pericardium, as will be described in more detail below. Illustrative variations of tissue-engaging members that may be advanced through a lumen (e.g., a sheath lumen and/or a tissue-piercing member lumen) are shown in FIGS. 3A-3H. FIG. 3A depicts a first variation of tissue-engaging member (304). As shown there tissue-engaging member (304) has a distal end (305) is at least in part in the form of a hook, and is sized and configured to be advanced at least partially through a first lumen (not shown) of a tissue-piercing member (302) (e.g., a multi-lumen needle). Tissue-engaging member (304) may be slideably held within the first lumen of tissue-piercing member (302) such that the distal end (305) tissue-engaging member (304) may be advanced or withdrawn relative to the tissue-piercing member (302). When the distal end (305) of tissue-engaging member (304) is advanced beyond the distal end of the tissue-piercing member (302), the hooked portion of distal end (305) may engage and manipulate the pericardium, as will be explained in more detail below.

Figure 3B:
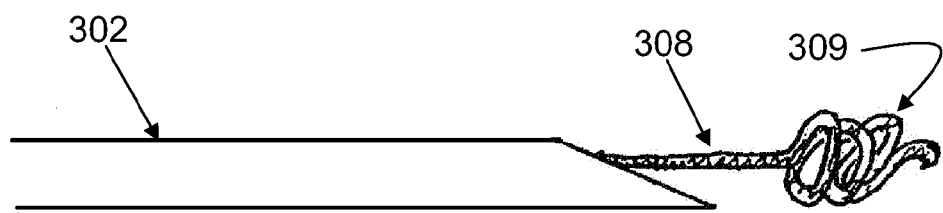
Figure 3C:
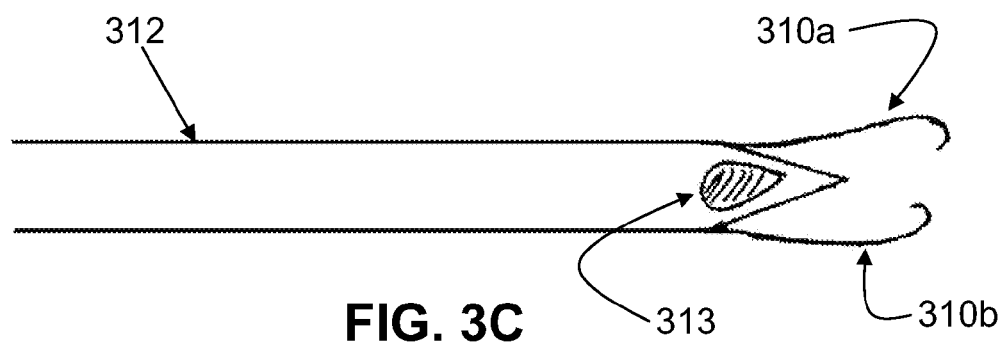

While shown in FIG. 3A as having a hooked distal end (305), the tissue-engaging members may have any suitable structure or structures capable of engaging pericardial tissue. For example, the distal end of the tissue-engaging members may also be in the shape of one or more corkscrews, such as tissue-engaging member (308) shown in FIG. 3B, which comprises a corkscrew tissue-engaging element (309) at its distal end. Tissue-engaging member (308) may be slidable disposed in a first lumen of tissue-piercing member (302). Rotating the corkscrew tissue-engaging element (309) of a tissue-engaging member (308) may cause the tissue-engaging member (308) to engage pericardial tissue and screw into the pericardial tissue. In other variations, a tissue-engaging element may comprise a plurality of tissue-engaging elements at a distal portion of the tissue-piercing member. Another variation of a tissue-engaging member is shown in FIG. 3C, where the tissue-engaging member comprises two tissue-engaging elements (310*a*) and (310*b*) that are shaped like antennae. The tissue-engaging elements (310*a*) and (310*b*) may be advanced through two longitudinal lumens (not shown) in tissue-piercing member (312) (e.g., a needle) to engage tissue by hooking and/or gripping tissue between the tissue-engaging elements. The longitudinal needle lumens may be arranged parallel to a third lumen (313), through which one or more guide elements may be passed. Tissue-engaging members may also comprise one or more grapnel tissue-engaging elements that may be advanced through a tissue-piercing member via one or more longitudinal lumens.

The distal ends of the tissue-engaging members described hereinthroughout may change between a low-profile configuration when passing through a lumen of a tissue-piercing member or sheath, and an deployed configuration when advanced out a distal end of the tissue-piercing member. Having a collapsed, compressed, or narrow profile, may facilitate movement of the tissue-engaging member as it is advanced through the lumen of the tissue-piercing member. After the distal of the tissue-engaging member has exited the lumen, e.g., at the distal end of a tissue-piercing member, it may assume a curved, expanded, or enlarged profile (e.g., as depicted in FIGS. 3A-3C for tissue-engaging member (304), tissue-engaging member (308), and tissue-engaging elements (310*a*) and (310*b*)). One or more portions of the tissue-engaging members may be made of a super-elastic or shape-memory material such as a nickel titanium alloy, which may be straightened or otherwise constrained in a lumen of a tissue-piercing member, and assume its deployed shape upon deployment. In some variations, there may be additional actuating mechanisms that may urge a tissue-engaging member from an undeployed configuration to a deployed configuration. For example, a tissue-engaging member may comprise multiple articulating segments that are generally straight during delivery through a lumen, and may be transitioned to a curved shape by actuating a mandrel that couples the segments to each other. Alternatively, tissue-engaging members may be advanced through a lumen of a tissue-piercing element (302) in the configuration that is already suitable for engaging tissue, and need not assume a separate configuration upon deployment.

Figure 3D:
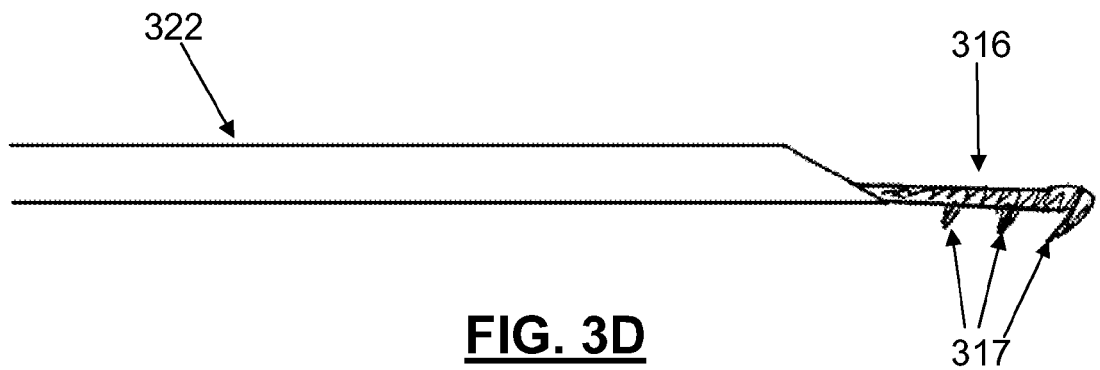

FIG. 3D depicts another variation of a tissue-engaging member (316) where the distal end is at least in part in the form of a sawtooth. Specifically, the tissue-engaging member (316) may advanceable through a first lumen of tissue-piercing member (322) (as described above), and may comprise a plurality of teeth (317) (e.g. 1, 2, 3, 5, 10, etc.), as desired for engaging pericardial tissue. Certain variations of a tissue-engaging member may comprise a plurality of tines, which may engage pericardial tissue as the tines are drawn across the pericardial surface. The tissue-engaging member (316) may be advanced through a second lumen of the needle (322), while a guide element may be advanced through a first lumen of the needle (not shown). The tissue-engaging member (316) may engage tissue by advancing the teeth (317) across the surface of the pericardium, and then retracting or otherwise withdrawing the tissue-engaging member (316) to cause the teeth (317) to dig into, secure or otherwise engage the pericardium. The teeth (317) may assume an undeployed configuration as it is being advanced through, and constrained by, the second lumen of the needle (322), and a deployed configuration as it exits the needle lumen. In the undeployed configuration, the teeth (317) may be compressed along the contour of the tissue-engaging member so that it may easily pass through the lumen of the needle (322). In the deployed configuration, the teeth (317) may protrude from the tissue-engaging member (316). In some variations, the teeth may be made of a super-elastic or shape-memory material, such as a nickel titanium alloy, or polymers such as polyethylene, nylon, polypropylene, PVC, and the like, while in other variations, the teeth may be made of a non-elastic biocompatible material, such as stainless steel, cobalt alloys (e.g. nickel-cobalt, cobalt-nickel-chromium-molybdenum), etc. Teeth that are made of a super-elastic or shape-memory material may reversibly or irreversibly transition from the undeployed to deployed configuration without additional actuation. For example, the tissue-engaging member and/or teeth may naturally have an expanded configuration, where the teeth protrude from the tissue-engaging member, and are only in a compressed configuration when constrained in the needle lumen. Once released from the lumen, the tissue-engaging member and/or teeth automatically assume its expanded configuration. In other variations where the tissue-engaging member and/or teeth are made from a non-elastic material, the teeth may transition from an undeployed configuration to a deployed configuration (e.g., from a collapsed and/or compressed undeployed configuration to an expanded deployed configuration) by using additional actuating mechanisms. For example, each of the teeth may be attached to the tissue-engaging member by a hinge, where in the undeployed configuration, the teeth are rotated inward, towards the longitudinal axis of the tissue-engaging member, and in the deployed configuration, the teeth are rotated outward, away from the main axis of the tissue-engaging member. The teeth may be configured, however, to rotate beyond a certain point relative to the main axis, such that the teeth may resist being hyperflexed when engaging tissue. Other suitable mechanical configurations may be used to aid in the deployment of the teeth (317).

Figure 3E:
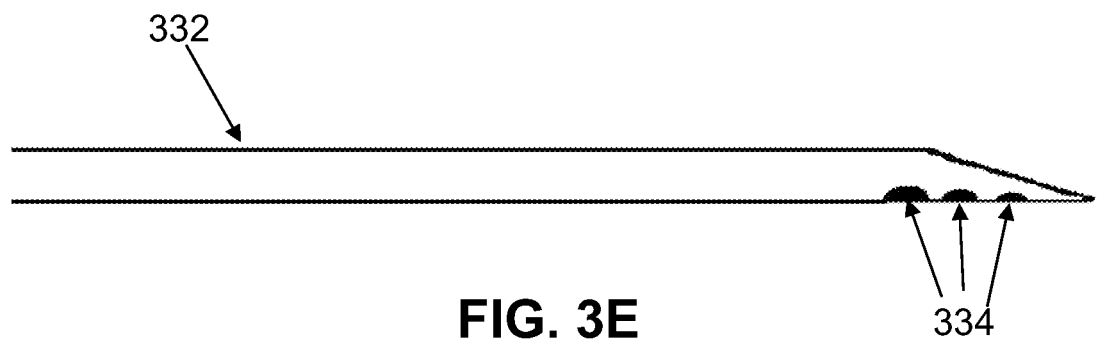
Figure 3F:
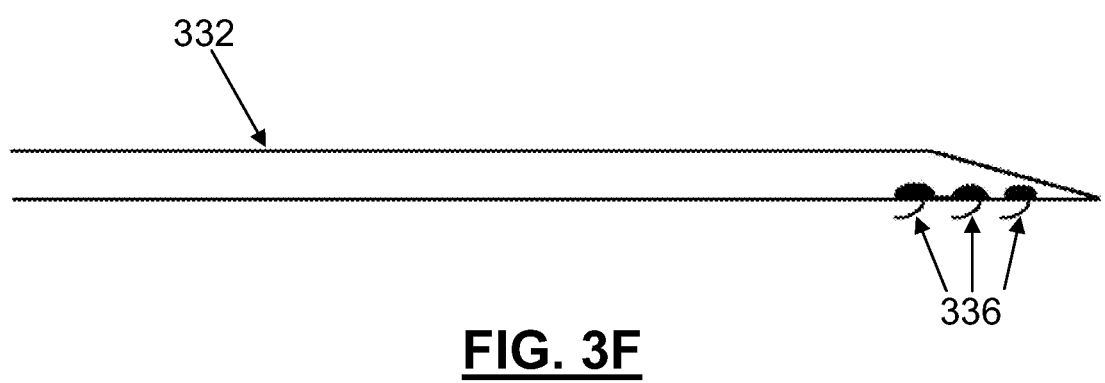

Another variation of a tissue-engaging member is shown in FIGS. 3E and 3F. As shown there, a tissue-piercing member (332) (e.g., a needle) may comprise one or more side apertures (334) at a distal location and at least one lumen therethrough, where the side apertures (334) and the lumen are in communication with each other. A tissue-engaging member with brush-like characteristics, such as teeth (336) may be advanced through the at least one lumen in an undeployed, collapsed configuration, where the teeth (336) are retracted, as previously described. Once the tissue-engaging member is fully advanced, it may be urged into a deployed, expanded configuration, as seen in FIG. 3F, where the teeth (336) protrude through the side apertures (334) to engage pericardial tissue, as will be described in more detail below. Additionally, while shown in FIGS. 3E and 3F as extending through side apertures (334) of a tissue-piercing member (332), teeth (336) of the tissue engaging member may additionally or alternatively be configured to extend through one or more side apertures (not shown) of a sheath or other catheter, as described in more detail below).

Figure 3G:
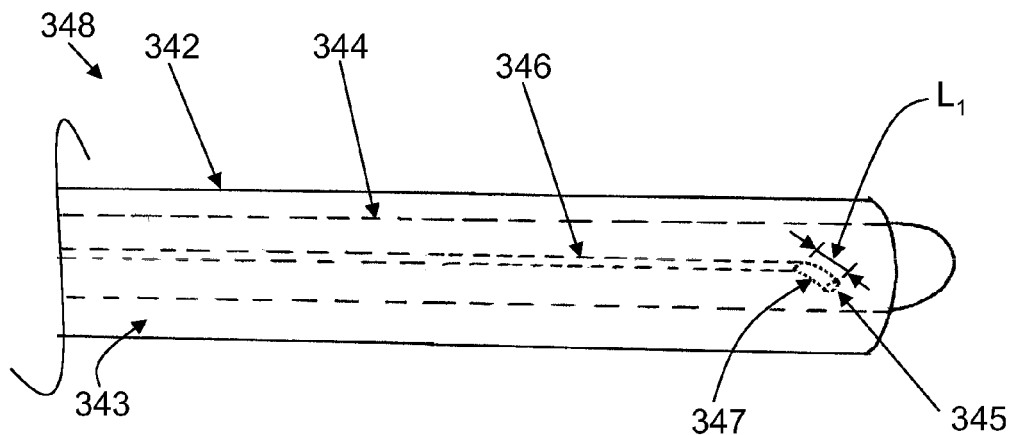

In some variations, a tissue-engaging member may also act as a tissue-piercing member to pierce the pericardium. For example, in FIG. 3G depicts another variation of a tissue-engaging member which may be used with an access device (348) to access a pericardial space of a heart. As shown there, the device (348) comprises a sheath (342), a catheter (344), and a tissue-engaging member, e.g., a barb (347) extending from catheter (344). The barb (347) may be connected to or integrally formed with catheter (344), and may comprise a barb lumen (345) continuous with the catheter lumen (346) such that a guide element (not shown) or one or more fluids may be passed through catheter lumen (346) and out of barb lumen (345). The barb (347) may protrude from the catheter (344) at an angle with respect to the outer surface of the catheter. For example, the barb (347) may protrude nearly perpendicularly to the surface of the catheter, or may protrude nearly tangentially, or at any angle between, such as about 1°-30°, or about 20°-30°, or about 30°-50°, or about 40°-70°, or about 65°-90°, or more than 90°. When catheter (346) is moved relative to the pericardium (e.g., by lateral motion, rotation, or the like), the distal-most tip of the barb (347) may be able to engage tissue, e.g., by hooking or piercing, and/or be configured to intimately contact tissue. The length ($L_1$) of the barb (347) may be determined in part by the thickness of the pericardial tissue. For example, the length ($L_1$) may be chosen to help ensure that the pericardium is engaged without piercing or damaging the heart, and may be from about 0.1 millimeter to about 12 millimeters, e.g., 0.1 millimeter to 10 millimeters, or 6 millimeters to 12 millimeters. Some variations of the barb (347) may have a length ($L_1$) that approximates the thickness of the pericardium, for example, from about 0.2 millimeters to about 7 millimeters. The catheter (344) may be slidably encased within the lumen (343) of the sheath (342). The sheath (342) may be actuated from a proximal portion, for example, using a handle actuator, to extend over the barb (347), e.g., to cover the barb (347) which may help prevent tissue from inadvertently engaging with the barb, and/or may be retracted from the barb (347), e.g., to expose the barb (347) to engage tissue. In some variations of the device (348) shown in FIG. 3G, the entire device may be rotated or twisted around its longitudinal axis. Methods of using the device (348) will be described below.

Figure 3H:
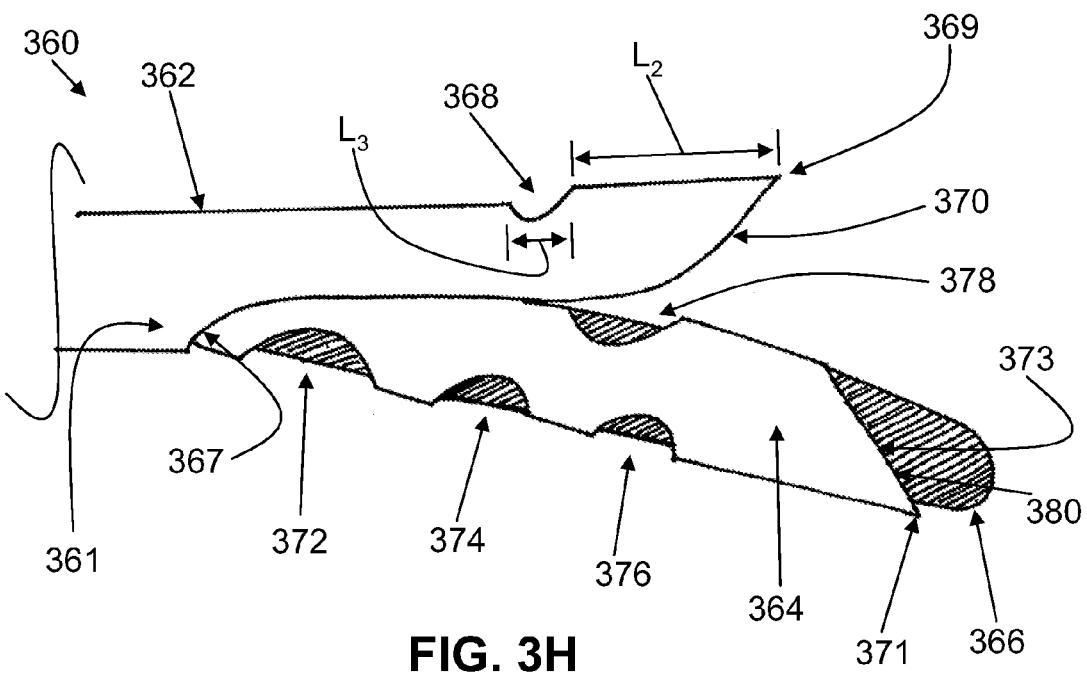

FIG. 3H illustrates another variation of an access device (360) in which a tissue-engaging member may also act as a tissue-piercing member. The distal portion of another variation of an access device (360) comprising a tissue-engaging element to access the pericardial space is shown in FIG. 3H.

As shown there, the device (360) comprises engagement element (362), and an inner tubular body (364). The engagement element (362) may have a longitudinal lumen (361) that extends at least partially therethrough, and inner tubular body (364) may be housed in or otherwise extend at least partially through lumen (361). The inner tubular body (364) may in turn have a longitudinal lumen (373) extending therethrough. The longitudinal lumens (361, 373) may have a closed-shape, e.g., entirely enclosed in the engagement element (362) or the inner tubular body (364), or may be an open-shape, e.g., C-shaped, as suitable for one or more devices to be advanced therethrough. While the engagement element (362) and the inner tubular body (364) described here each have one longitudinal lumen therethrough, it should be understood that they may each have additional longitudinal lumens as desired, and may be configured as described in more detail above. For example, additional lumens may be provided in the engagement element (362) and/or the inner tubular body (364) for drug delivery, contrast agent infusion, guide wire delivery, device delivery, etc., where each lumen may be used for one or more functions.

As seen in FIG. 3H, the longitudinal lumen (361) terminates at an aperture (367) extending from the distal tip (369) of the engagement element (362). In other variations, the aperture may be located entirely in a sidewall of the engagement element (362) but in other variations. The aperture (367) may be set at an angle with respect to the main longitudinal axis of the engagement element (362), or may be parallel or concentric with the engagement element and/or the longitudinal lumen (361). The distal tip (369) may have one or more features that are able to puncture or pierce heart tissue. For example, as depicted in FIG. 3H, the distal tip (369) is pointed, but may additionally or alternatively be sharpened, beveled, or angular as suitable for creating a puncture or slit in the pericardium. In some variations, the geometry of the engagement element (362) may comprise one or more curves, for example, the rounded edge (370). The rounded edge (370) may have any suitable geometry or radius of curvature that may promote atraumatic tissue contact. For example, the rounded edge may have a taper or curve that corresponds to one or more curves of the heart, or may be a portion of an oval or ellipse, such that the pericardium may be engaged and punctured while minimizing the risk of puncturing the heart. The engagement element (362) may also comprise one or more grooves (368) that are located a length ($L_2$) away from the distal tip (369). The length ($L_2$) may be from about 2 millimeters to about 3 millimeters. For example, the length ($L_2$) may be chosen so that the distal tip (369) may puncture only the pericardium, without piercing or puncturing the heart. The groove (368) may have a length ($L_3$), where ($L_3$) may be from about 1 millimeters to about 2 millimeters. For example, the length ($L_3$) may be determined in part by the thickness of the pericardium, from about 1.5 millimeters to about 4.5 millimeters. When tissue-engaging member (362) is advanced into pericardial tissue, as described in more detail below, the grooves (368) may act to catch or otherwise engage the pericardial tissue, which may act to limit the depth of penetration by tissue-engaging member (362) and/or lift the pericardium relative to the heart. In some variations, the maximum puncture depth may be determined in part by the length ($L_2$).

The inner tubular body (364) may comprise one or more side apertures (372, 374, 376, and 378) and/or a distal aperture (380) in communication with the lumen (373), and a sharpened tip (371). In some variations, the inner tubular body (364) may be a needle, where the sharpened tip (371) may help to puncture, pierce, or create a slit in the pericardium. The lumen (373) may be sized and shaped for passing a guide element, e.g. guide wire (366), therethrough. In some variations, the lumen (373) may comprise features that may help ease the passage of the guide wire (366) therethrough, for example, friction-reducing coatings, curves that correspond with the curvature of the guide wire, etc. Alternatively or additionally, the lumen (373) may be configured for the delivery of various fluids. For example, any suitable gas (e.g., carbon dioxide, oxygen, nitrogen, or a blend of gases) may be delivered through the lumen to insufflate the pericardial space, and/or any liquid fluids such as therapeutic agents, rinse agents, and/or imaging contrast agents may also be delivered. Inner tubular body (364) need not comprise any side apertures, but in variations where inner tubular body (364) comprises one or more side apertures, there may be any number of side apertures (e.g., 1, 2, 4, 7, 10, etc.) sized and shaped for the delivery of any desired fluids. For example, while shown in FIG. 3H as being generally circular, the side apertures (372, 374, 376, and 378) may be any suitable shape (e.g., may be rectangular, hexagonal, etc., and/or may be slits), as appropriate for the effective delivery of the desired fluid therethrough. In some variations, a distal portion of the inner tubular body (364) may be made of a mesh material, which may allow for the release of fluids along the distal portion. The various components of the device (360), such as the engagement element (362) and the inner tubular body (364) may be made of any biocompatible material, such as nylon, PEBAX, polyimide, PEEK, Nitinol, and the like.

The advancement and deployment of the tissue-engaging members shown in FIGS. 3A-3H may be controlled by a proximally-located actuator. In some variations, the actuator that controls the tissue-engaging member may also control one or more other components of the access device (e.g., a tissue-piercing member, a sheath, etc.). When a tissue-engaging member engages the pericardium and/or manipulates it in a particular fashion, such engagement and manipulation is controlled by an actuator. For example, the actuator may be configured to move the tissue-engaging member relative to a tissue-piercing member or a sheath to move the tissue-engaging member between a low-profile, undeployed configuration and a deployed configuration. The actuator may further be configured to move the tissue-engaging member or members in a rotating motion (e.g., corkscrew member, or barbed catheter), a lateral motion (e.g., sawtooth), a twisting motion, combinations thereof, and the like. In some variations, the pericardium may be additionally manually manipulated by a practitioner or mechanically manipulated by a practitioner and/or a machine.

In some variations, one or more surfaces of the tissue-engaging members may be modified to enhance the frictional contact or other engagement with pericardial tissue. For example, in some variations tissue-engaging members may have textured surfaces (e.g., striped, grooved, checked, hooked, looped, etc.), so as to increase the surface area contact with the pericardial tissue. Tissue-engaging members may also comprise one or more friction-enhancing surface coatings on the tissue-engaging elements, to help ensure a firm and secure interaction with the pericardium. In some variations, the coating may also create a textured surface (e.g., striped, grooved, checked, hooked, looped, etc.) to increase the surface area of the tissue contact region. Alternatively or additionally, the surface of the tissue-engaging member and elements may be modified with any material that may help to encourage adhesion or other attractive interactions between the tissue-engaging element and the pericardium. For example, the material may have an adhesive surface that may engage the pericardium by hydrophobic or hydrophilic interactions, and may be configured to form temporary or permanent bonds with the pericardium. Examples of such materials include polymer bonding agents, such as acrylics, anaerobics, cyanoacrylates, epoxies, hot melts, silicones, urethanes and UV/light curing adhesives and the like, biocompatible friction particles and liquid resins, cellulose fiber, ceramic fiber, cotton fiber, mica, vermiculate, elastomeric materials like silicone, latex, polyisoporene or rubber, etc. In some variations, the surface may be modified with antigens or receptors that bind to receptors or antigens that are present on the surface of the pericardium, which may help the tissue-engaging element attach to the pericardium.

Some variations of tissue-engaging members and/or elements may be at least partially made of electrically conductive materials, and may be used to obtain electrophyiological measurements, as well as apply an electrical current to tissue or create an electric field in the tissue. Electrical currents may be applied as part of a treatment for fibrillating cardiac tissue, or may be used to ablate tissue. Electric fields or potentials may applied for stimulating cardiac tissue. For such variations, tissue-engaging members and elements may have a certain geometry to attain a desired current-density at the junction between the tissue-engaging member and the cardiac tissue surface. For example, the contact area between the tissue-engaging member and the tissue surface may be increased (e.g., to decrease current density), or decreased (e.g., to increase current density). There may also be tissue-engaging members that act as a current source or current sink that may provide a path for an injected current, and/or provide a reference ground for any electrical measurements. Biocompatiable electrode materials that may have suitable electrical properties for the above mentioned functions may include metallic materials, such as platinum, iridium, rhodium, gold, palladium, various platinum alloys (e.g. platinum-iridium), stainless steel (e.g. 316LVM), cobalt alloys (e.g. nickel-cobalt, cobalt-nickel-chromium-molybdenum, etc). Electrodes may be coated with silver-chloride, iridium-oxide, etc. as appropriate. In other variations where electrical stimulation or measurement is undesired, the tissue-engaging members and/or elements may be made of non-conductive or insulating materials, such as polycarbonate, Ultem® (polyetherimide), PEEK, Teflon®, etc., which may be electrically neutral.

II. Methods

Methods of accessing the pericardial space are also provided here and may use one or more of the devices described above. One example of a method (400) that may be used to access a pericardial space of a heart is shown as a flowchart in FIG. 4A. The heart and surrounding pericardial structures may first be imaged (401) using any appropriate imaging modality, e.g., direct visualization, fluoroscopy, endoscopy, echocardiography or any combinations thereof. Some or all of the steps of the methods described here may be performed under visualization using one or more of these imaging modalities, and one or more portions of the devices may be configured for viewing using one or more of these modalities. A tissue-piercing member, e.g., a needle, may be advanced towards the surface of pericardium (402) under image guidance. The tissue-piercing member may be introduced using known percutaneous and/or minimally invasive techniques. In some variations, a sheath (for example, sheath (208) or sheath (902) may first be placed into the body (e.g., beneath the sternum), and the tissue-piercing member may be advanced through at least a portion of the sheath. As the tissue-piercing member is advanced toward the pericardium, the distal end of the tissue-piercing member may be placed at or near the surface of the pericardium. For example, in some variations, the distal end of the tissue-piercing member may be positioned near the pericardium without touching the pericardium. In other variations, the distal end of the tissue piercing member may be positioned such that it is in contact with one or more portions of the pericardium. Positioning of the tissue-piercing member may be confirmed and/or guided in any suitable manner, such as one or more of the imaging modalities mentioned above. In variations where the tissue-piercing member is positioned such that it is in contact with one or more portions of the pericardium, positioning may be confirmed and/or guided by tactile feedback of the tissue-piercing member.

Once the tissue-piercing member has been positioned relative to the pericardium, one or more tissue-engaging members may be deployed to engage the tissue of the pericardium (404). The tissue-engaging member and/or the tissue-piercing member may then be moved or otherwise manipulated in order to manipulate the pericardium for piercing (406). For example, the tissue-engaging member and/or tissue-engaging member may be moved or otherwise actuated to separate the pericardium from the heart to locally enlarge the pericardial space, as described in more detail below. Additionally or alternatively, fluid insufflation may also be used to enlarge a portion of the pericardial space, as will be described in more detail below. Positioning of the pericardium may be confirmed in any suitable manner, such as those described above.

Once the engaged pericardium has positioned as desired, the tissue-piercing member may be advanced or otherwise manipulated to puncture the pericardium and enter the pericardial space (408). Access to the pericardial space via the needle may be confirmed (410) (e.g., using visualization and/or introducing one or more contrast solutions into the pericardial space via the tissue-piercing member), the distal end of a guide element such as those described above (e.g., a guide wire) may be advanced into the pericardial space (411). The guide element may be advanced by manually by a practitioner, or mechanically by an actuating mechanism that may be activated by a practitioner. For example, the guide element may be advanced by gear-driven or spring mechanisms that may be activated by the practitioner. The advancement of the guide wire may be user-controlled or machine-controlled, where the movement of the guide wire may be pre-programmed into a computing device. In some variations, user-controlled advancement of the guide wire may be manual, where the user directly advances the guide wire, e.g., by directly pushing the guide wire. Additionally or alternatively, user-controlled advancement may be automatic, where the user actuates a mechanism that in turn, advances the guide wire. Examples of automatic mechanisms include gear-drives, spring mechanisms, and the like. Optionally, a contrast agent or other fluid may be infused into the pericardial space as the guide wire is advanced. The contrast agent may be infused before and/or after the guide wire is advanced into the pericardial space, and in some variations, may be infused concurrently with the advancement of the guide wire. Additionally or alternatively, the guide wire may comprise one or more depth marker that may indicated the depth of advancement of the guide wire.

Once a guide element has been placed at least partially into the pericardial space, one or more portions of the access device (e.g., a tissue-piercing member, a tissue-engaging member, or the like) may be removed, leaving the guide element in place. The guide element may help to provide an access route to the pericardial space for one or more other devices. In some variations, one or more dilators may be advanced over the guide element to guide or otherwise place a catheter or other device into the pericardial space. Additionally or alternatively, one or more additional devices (e.g., electrode leads, ablation devices, etc.) may be then advanced over, along, or through the guide element to access the pericardial space, where one or more procedures may be performed via the pericardial access. Examples of such procedures include, but are not limited to, left atrial appendage closure, drug or implant delivery, one or more ablation procedures, valve repair, or the like. It should also be appreciated that in variations where an access device comprises a sheath, the sheath may at least temporarily remain in place to help aid in advancement of the additional devices over, along, or through the guide element.

Figure 4A:
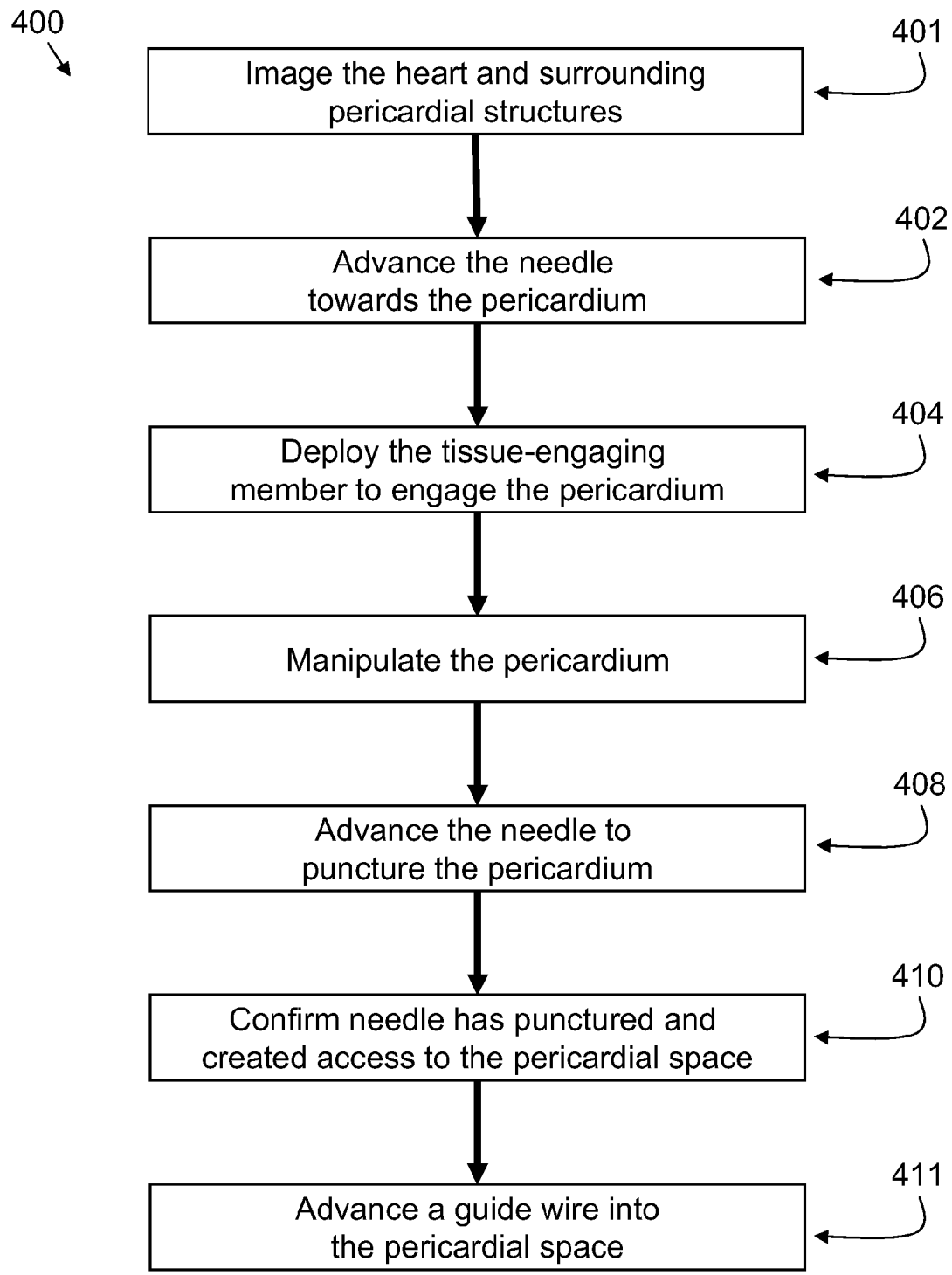
FIG. 4A depicts, in flowchart form, one variation of a method that may be used to access the pericardial space of a heart.
Figure 4B:
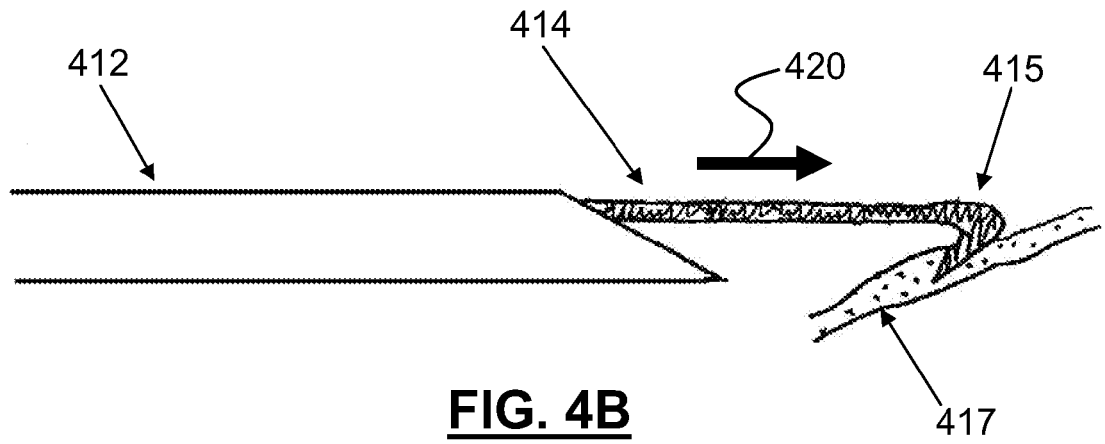
FIGS. 4B-4D illustrate one way in which the device of FIG. 3A may be used with the method of FIG. 4A.
Figure 4C:
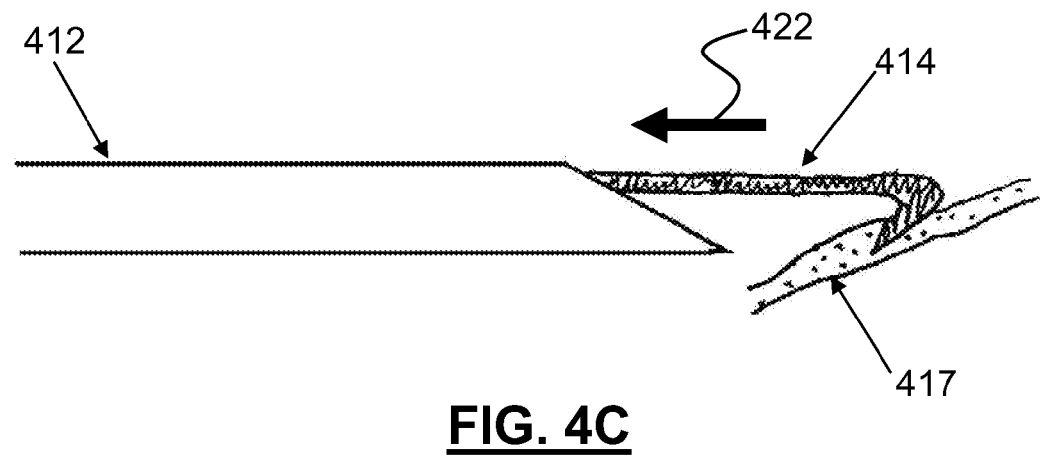
Figure 4D:
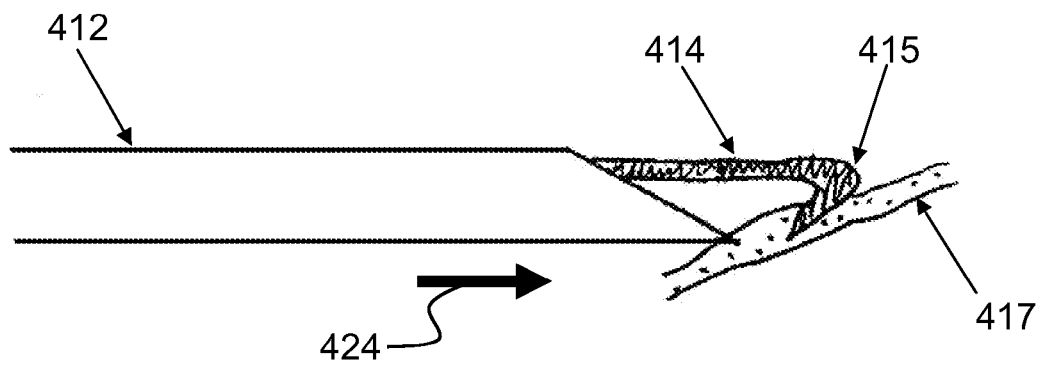

FIGS. 4B-4D illustrate one way in which the tissue-engaging member of an access device, such as the device described and shown in FIG. 3A, may be used with the method (400) depicted in flowchart form in FIG. 4A. Specifically, needle (412) may be advanced toward the pericardium (417) in any manner described above, as shown in FIG. 4B. While shown in FIGS. 4B-4D as comprising a needle (412), the access devices may include any of the tissue-piercing members described above. Additionally, while shown in FIG. 4B as being advanced near the pericardium (417) without contacting the pericardium (417), it should be appreciated that in some instances the needle (412) may be advanced such that at least a portion of the needle is in contact with the pericardium (417).

Once in place, a hooked distal end (415) of tissue-engagement member (414) be advanced out of a lumen (not shown) of needle (412), and advanced towards the pericardium (417) in the direction of arrow (420), as illustrated in FIG. 4B, and may be manipulated such that it engages with the pericardium (417). While shown in FIG. 4B as having a hooked distal end (415), it should be appreciated that the tissue-engaging member (414) may be any suitable tissue-engaging member as described hereinthroughout. Once the pericardium is engaged by the hooked distal end (415), the tissue-engaging member (414) may be withdrawn in the direction of arrow (422), as shown in FIG. 4C. This may act to pull the pericardium (417) away from the surface of the heart (not shown), which may increase the distance between a portion of the pericardium and the heart. In some instances, the needle (412) and tissue-engaging member (414) may be withdrawn simultaneously. In other instances, the tissue-engaging member (414) may be withdrawn relative to needle (412) such that distance between the pericardium (417) and the needle (412) is decreased. In some of these variations, withdrawal of the tissue-engaging member (414) may pull pericardium (417) against the needle (412) such that the needle punctures or otherwise penetrates tissue. In other variations, the needle (412) may be advanced relative to tissue-engaging member (414) and pericardium (417) in the direction of arrow (424) to puncture the pericardium (417), as shown in FIG. 4D. It should also be appreciated in some variations, the tissue-engaging member (414) may be withdrawn and the needle (412) may be advanced simultaneously to pierce tissue.

Figure 5A:
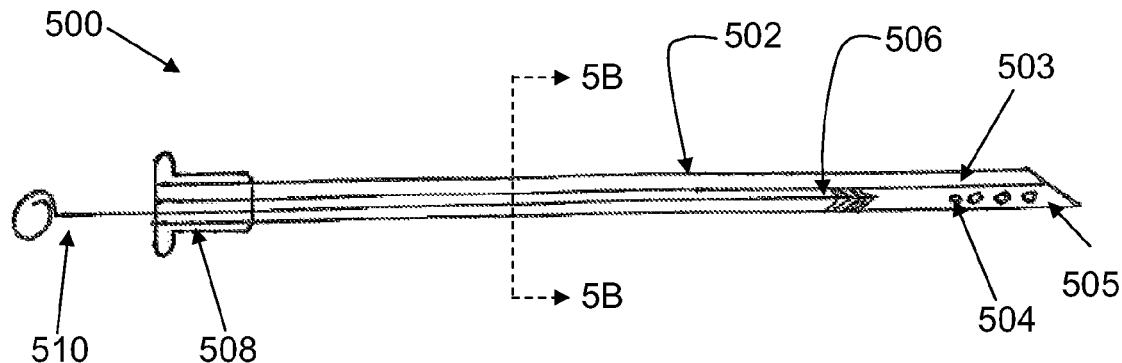

Another variation of a device and method for accessing a pericardial space of a heart is depicted in FIGS. 5A-5L. FIGS. 5A-5E show one variation of an access device (500) which may be used with a variation of method (400). Access device (500) comprises a tissue-piercing member, e.g., a needle (502), one or more tissue-engaging members, e.g., a tissue-engaging member (506), and a guide element (not shown), where the tissue-engaging member (506) and the guide element are housed within the needle (502). In this variation, the needle (502) may comprise a first longitudinal lumen (505) that is connected to one or more side apertures (504), and a second longitudinal lumen (503). A needle (502) may be moved and steered by a needle actuator (508), which may be located on a proximal portion of the needle. The tissue-engaging member (506) may be disposed in the first lumen (505) and advanced distally in an undeployed configuration, and may be moved and steered by the tissue-engaging member actuator (510). For example, the tissue-engaging member actuator (510) may be used to advance, retract, and/or deploy the tissue-engaging member (506). FIG. 5B depicts a cross-section taken along the dotted lines in FIG. 5A. As shown there, the first longitudinal lumen (505) is positioned below the second longitudinal lumen (503), where the first longitudinal lumen (505) is circular, and the second longitudinal lumen (503) is semi-circular. However, in other variations, the first and second longitudinal lumens may be arranged in other suitable configurations, and may be of different sizes and shapes. For example, both longitudinal lumens may be semi-circular, circular, rectangular, trianglar, hexagonal, or any other closed-shape. The longitudinal lumens in a needle may be different sizes from each other, or may be the same size. The size and shape of first longitudinal lumen (505) and second longitudinal lumen (503) may vary depending on the size and shape of the devices to be advanced through them. Optionally, the inner surface of the longitudinal lumens may be modified to facilitate the passage of devices therethrough. For example, the inner surface of the lumen may be modified to increase or decrease the resistance (e.g., friction) to the passage of devices therethrough. In some variations, the inner portion of the longitudinal lumens may comprise one or more grooves or protrusions that may interfit with one or more protrusions and grooves that may be on the device being advanced therethrough. For instance, the grooves or protrusions in the longitudinal lumen and the device may be configured so that when a protrusion on the device interfits with a groove in the lumen, the device location of the device may be secured. To advance the device further, an additional force may be applied so that the protrusion on the device may be disengaged from the groove in the lumen. There may be multiple grooves in the longitudinal lumen, so that the device may be advanced through the lumen in an incremental or step-wise fashion. The grooves or protrusions in the longitudinal lumen may be spaced in regular or irregular intervals, as desired.

Figure 5D:
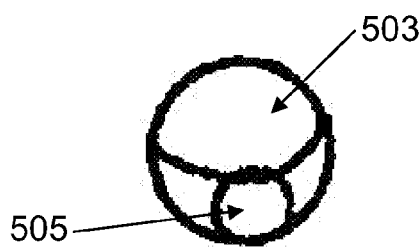
Figure 5D:
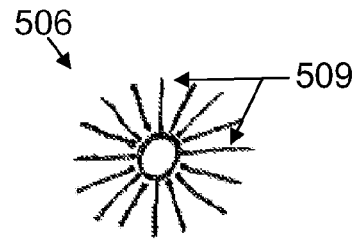
Figure 5D:
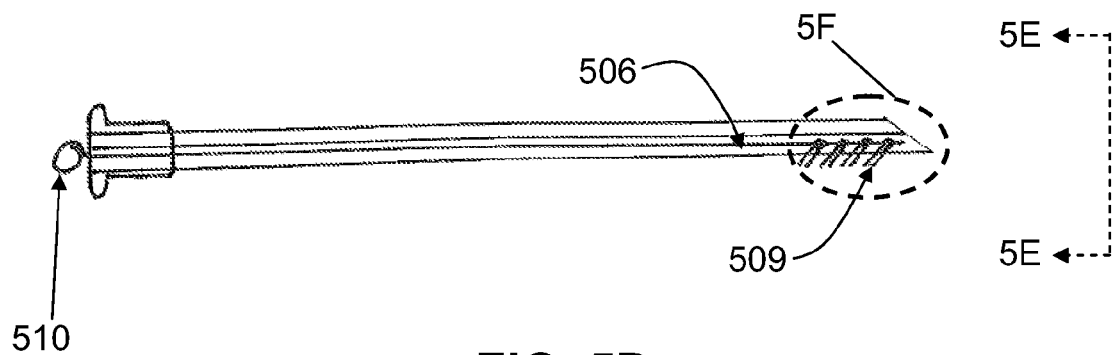

Turning back to the figures, tissue-engaging member (506) may comprise one or more tissue-engaging elements (509). The tissue-engaging elements (509) may comprise one or more barbs, prongs, spikes, or the like, and may be capable of moving between a low-profile, compressed configuration, and an expanded, deployed configuration. FIG. 5A shows a tissue-engaging member (506) in an undeployed configuration, where the tissue-engaging elements are compressed within the first lumen (505). FIG. 5C shows a cross-section of the tissue-engaging member (506) in a deployed configuration, where the tissue-engaging elements (509) are expanded. As seen in FIG. 5D, the individual tissue-engaging elements may extend through the side apertures (504) of needle (502) as the tissue-engaging member (506) is advanced forward in first lumen (505), while in other variations, the tissue-engaging member may be deployed after the tissue-engaging elements are advanced to a location outside of the first lumen (505). In these other variations, the needle (502) may not have side apertures (504) sized and shaped for passing tissue-engaging elements.

Figure 5E:
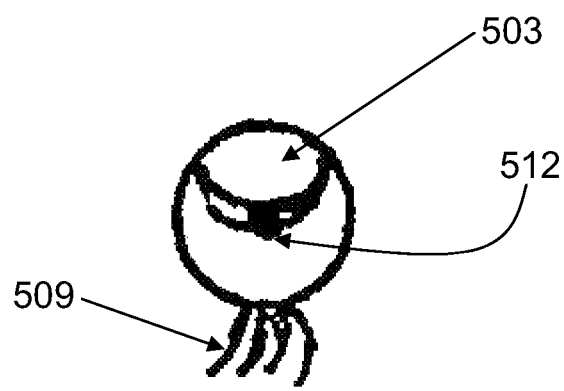
Figure 5F:
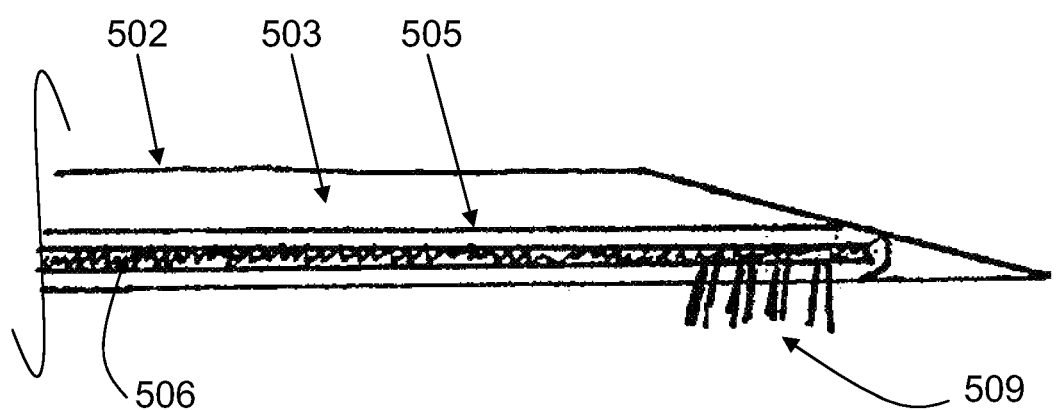

FIG. 5E depicts a front view of the distal end of device (500) along the dotted line in FIG. 5D, and FIG. 5F depicts a close-up view of the distal portion of the device (500). The needle (502) has a beveled distal tip (512), where the second lumen (503) terminates at an opening at the distal end, shown in FIG. 5E. The distal tip of other variations of needles or tissue-piercing members may have a tapered sharpened point, or other tip geometry. The first lumen (505) of the needle (502) remains entirely enclosed within the needle (see FIG. 5F), and tissue-engaging elements (509) in their deployed configuration exit first lumen (505) via side apertures (504). The tissue-engaging elements (509) may extend from first lumen (505) via side apertures (504) generally perpendicular relative to the longitudinal axis of the first lumen (505) (as shown in FIG. 5F), at an acute angle (as shown in FIG. 5D), or the tissue-engaging elements (509) may extend at a plurality of angles. As described previously, other variations of a needle may be used with method (400), where the longitudinal lumens of the needle may terminate at openings at the distal end. This may allow tissue-engaging members to pass through the distal tip of the needle.

Figure 5G:
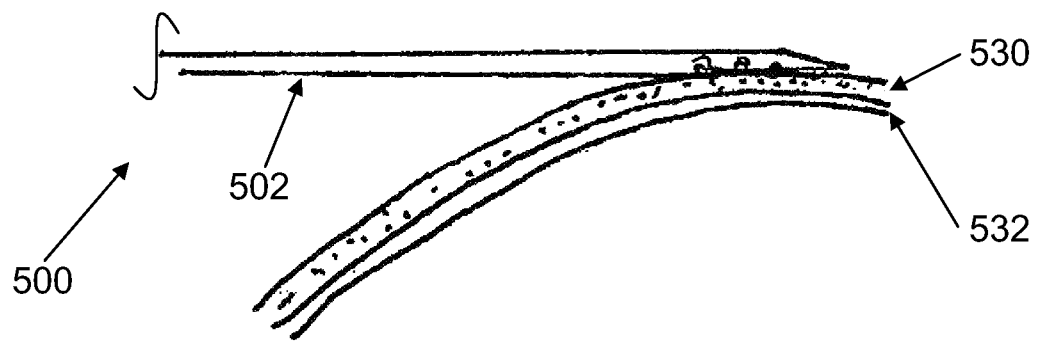
FIGS. 5G-5L depict the use of an access device to engage, manipulate, and penetrate the pericardium of a heart to access the pericardial space.
Figure 5H:
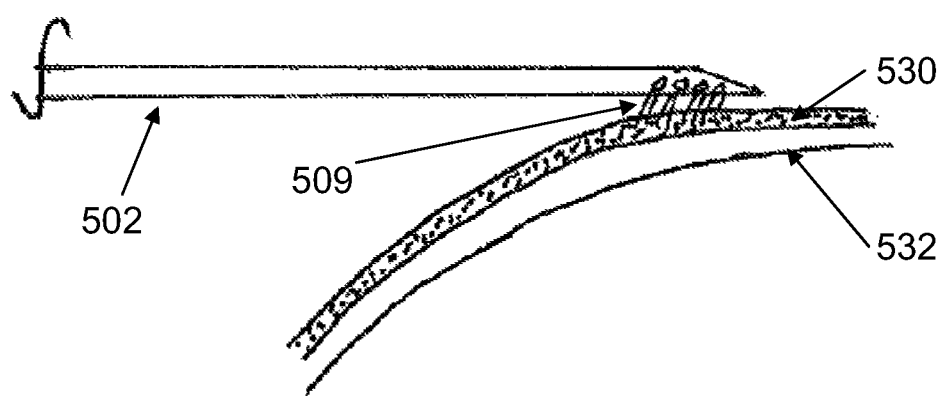
Figure 5I:
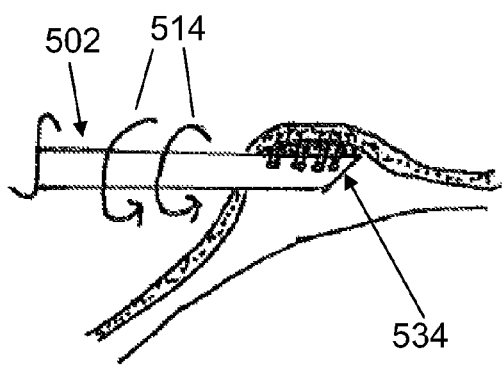
Figure 5J:
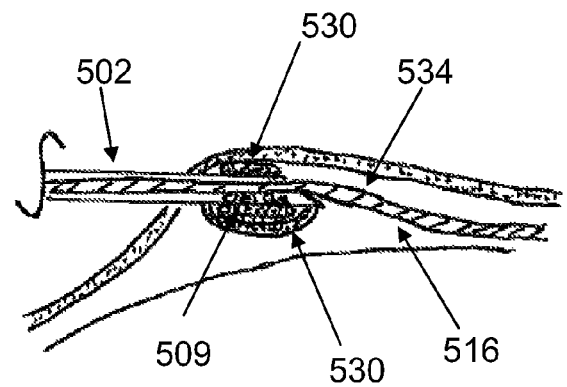
Figure 5K:
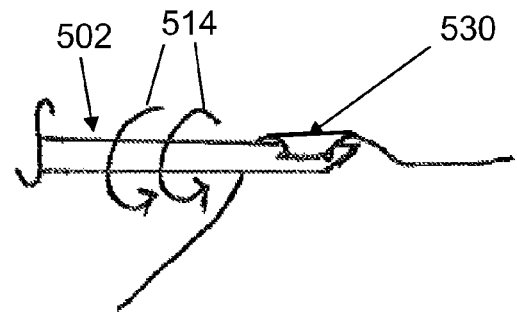
Figure 5L:
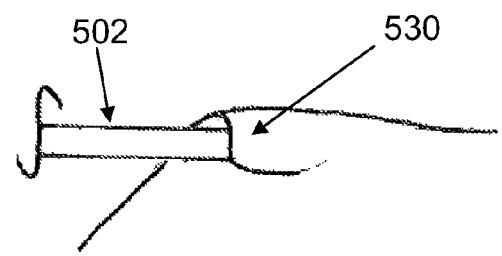

The device (500) may be used in accordance with one variation of the method (400) as illustrated in FIGS. 5G-5L. As shown in FIG. 5G, the needle (502) may be introduced towards the surface of pericardium (530) by any suitable technique. Depending on the variation of tissue-engaging member used and the properties of the pericardium (530), there may be direct contact between the needle (502) and the pericardium (530) as shown, or the needle (502) may be positioned in close proximity to the pericardium without directly contacting the pericardium. For example, the needle may be positioned tangentially to the surface of the pericardium. A tissue-engaging member actuator (510) may be actuated to advance and deploy the tissue-engaging member (506), such that the tissue-engaging elements (509) exit the side apertures (504), to engage a portion of the pericardium (530), as depicted in FIG. 5H. Once the pericardium has been engaged by the tissue-engaging member (506), the pericardium may be manipulated by the tissue-engaging member and/or needle. For example, the needle (502) may be rotated any number of degrees (e.g., 10°, 30°, 45°, 90°, 120°, 180°, 270°, 300°, 360°, etc.) according to arrows (514). Rotating needle (502) after engaging the pericardium may act to wrap the pericardium around the needle, as shown in a cross-sectional side view in FIG. 5I and a side view in FIG. 5K. This may help to increase the distance between a portion of the pericardium (530) the epicardial surface of heart (532), which may enlarge a region of the pericardial space (534). The enlarged pericardial space (534) may provide additional working volume for the advancement of devices towards the heart (532), such that the heart is not contacted by the tissue-engaging member (506) or needle (502). Generally, increasing the distance between the pericardium and the surface of the heart may help decrease the risk that the heart will be punctured when the pericardium is punctured. Once the pericardium (530) has been sufficiently wrapped around needle (502) and the pericardial space (534) has been sufficiently enlarged, the needle (502) may be advanced to pierce the pericardium (530) and enter the pericardial space (534), as shown in a cross-sectional side view in FIG. 5J and in a side view in FIG. 5L. Also shown there, a guide element, e.g., a guide wire (516), which may be housed in the second lumen (503), may be advanced into the pericardial space. Optionally, once access to the pericardial space via the guide wire (516) is established, the needle (502) may be withdrawn.

Figure 10A:
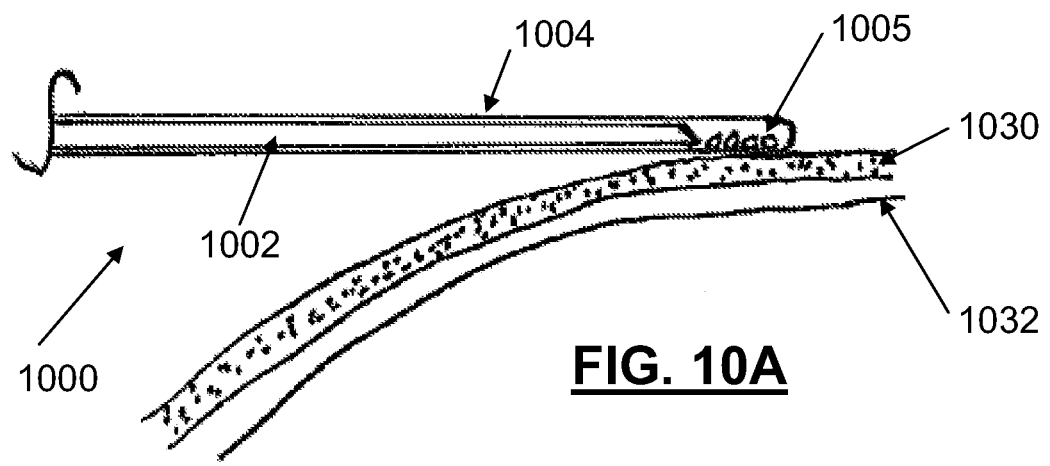
Figure 10B:
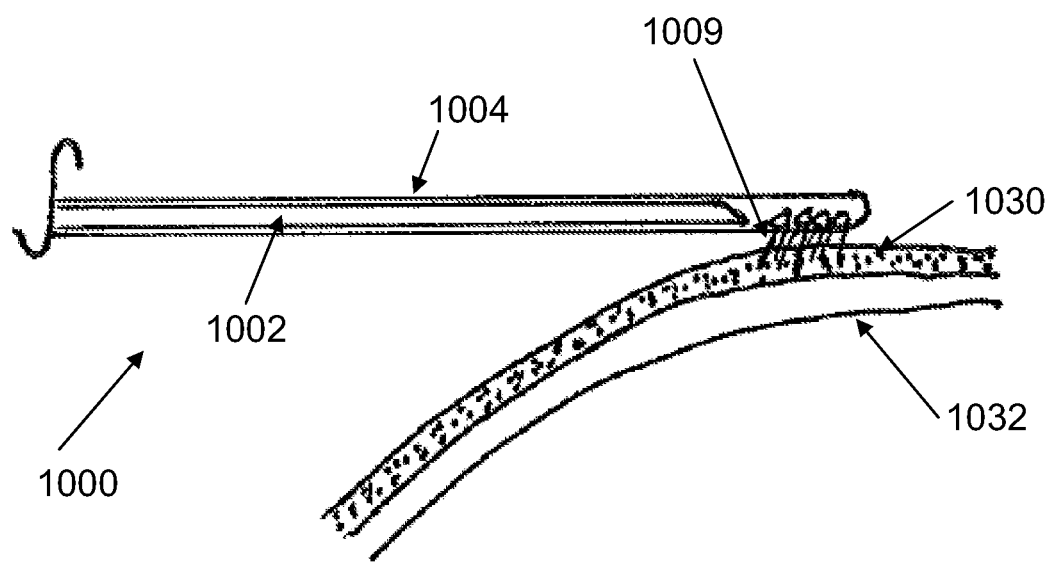
Figure 10G:
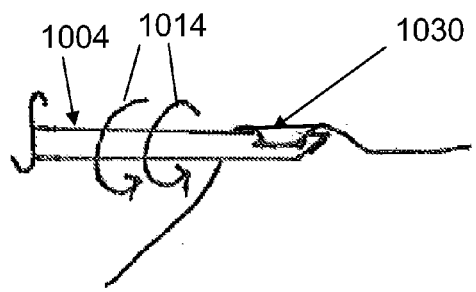
Figure 10G:
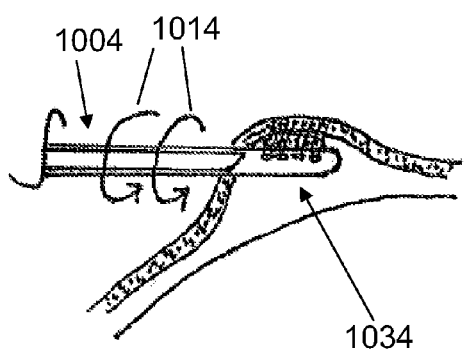
Figure 10G:
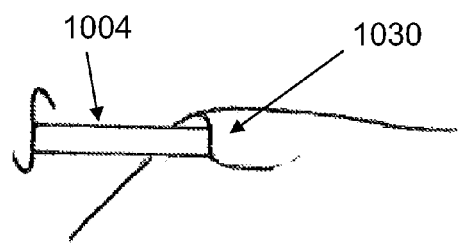
Figure 10G:
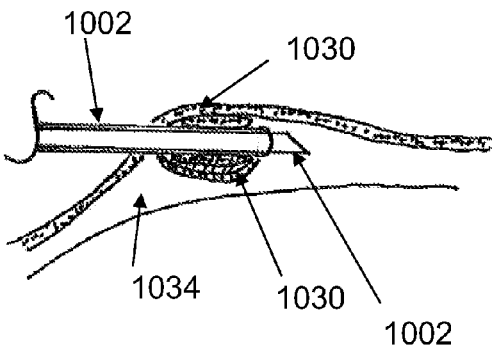
Figure 10G:
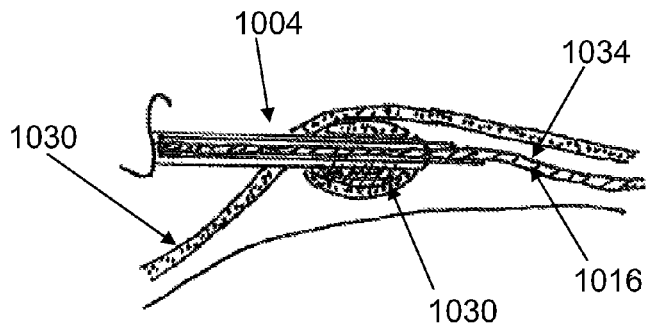

FIGS. 10A-10G illustrate a method by which a variation of access device (1000). As shown there, access device (1000) comprises a sheath (1004) comprising first and second longitudinal lumens (not shown) extending therethrough and a plurality of side apertures (1005) in communication with the second lumen. A tissue-piercing member (1002), such as those described above, may be advanceable through the first lumen, and a tissue-engaging member (not shown) may be advanceable through the second lumen, to allow one or more tissue-engaging elements (1009) to pass through the side apertures (1005). As shown in FIG. 10A, sheath (1004) may be introduced towards the surface of pericardium (1030) by any suitable technique. Sheath (1004) may be placed in direct contact with pericardium (1030), or may be positioned in close proximity to the pericardium (1030) without directly contacting the pericardium (1030). Once in place, the tissue engaging member may be actuated or otherwise advanced such that tissue-engaging elements (1009) exit the side apertures (1005), as shown in FIG. 10B. The sheath (1004) and tissue-engaging elements (1009) may be moved or otherwise manipulated such that the tissue-engaging elements (1009) engage the pericardium (1030).

Once the pericardium has been engaged by the tissue-engaging elements (1009), the pericardium (1030) may be manipulated by the tissue-engaging member and/or sheath. For example, the sheath (1004) may be rotated according to arrows (1014), as shown in a side view in FIG. 10C and a cross-sectional side-view in FIG. 10D. This rotation may act to wrap the pericardium (1030) around sheath (1004), which may help to increase the distance between the pericardium (1030) and the epicardial surface of heart (1032), which may enlarge a region of the pericardial space (1034). Once the pericardium (1030) has been wrapped around sheath (1004), tissue-piercing member (1002) may be advanced through the first lumen of sheath (1004) to puncture the pericardium (1030). Once tissue-piercing member (1002) has been advanced into the pericardial space (1034), a guide element (1016) (e.g., a guide wire) may be advanced through a lumen (not shown) in the tissue-piercing member to enter the pericardial space (1034). Sheath (1004) and/or tissue-piercing member (1002) may optionally be withdrawn, leaving guide element (1016) in place.

Figure 7A:
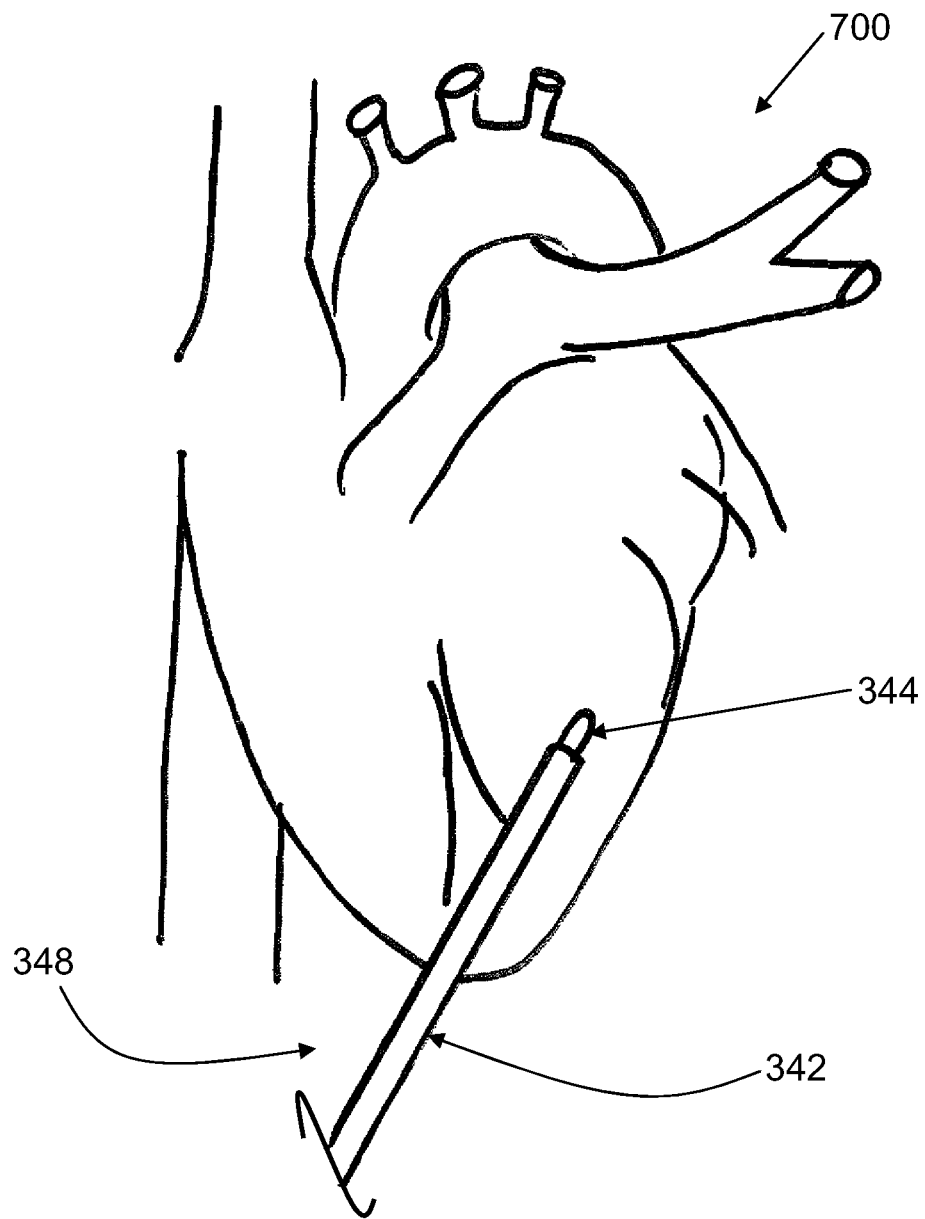
FIGS. 7A-7E illustrate another variation of a device and method that may be used to access the pericardial space of a heart.

Other devices may be used with a variation of the above-described methods to access the pericardial space. For example, the access device depicted in FIG. 3G may be used with the method illustrated in FIGS. 7A-7E. As shown in FIG. 7A, access device (348) may be inserted into a chest cavity (e.g., from a subxiphoid approach or another suitable approach) and advanced to the surface of a heart (700), to a region just outside of the pericardium. While shown in FIG. 7A as advanced simultaneously, it should be appreciated that sheath (342) and catheter (344) may be advanced sequentially. For example, sheath (342) may be advanced such that its distal end is positioned near the pericardium, and catheter (344) may then be subsequently advanced through (342). Generally, the barb (347) may be covered by sheath (342) during advancement and positioning of device (348). Advancement and/or positioning of the sheath (342) and/or catheter (344) may be done under and confirmed in any suitable manner, such as those described above.

Figure 7B:
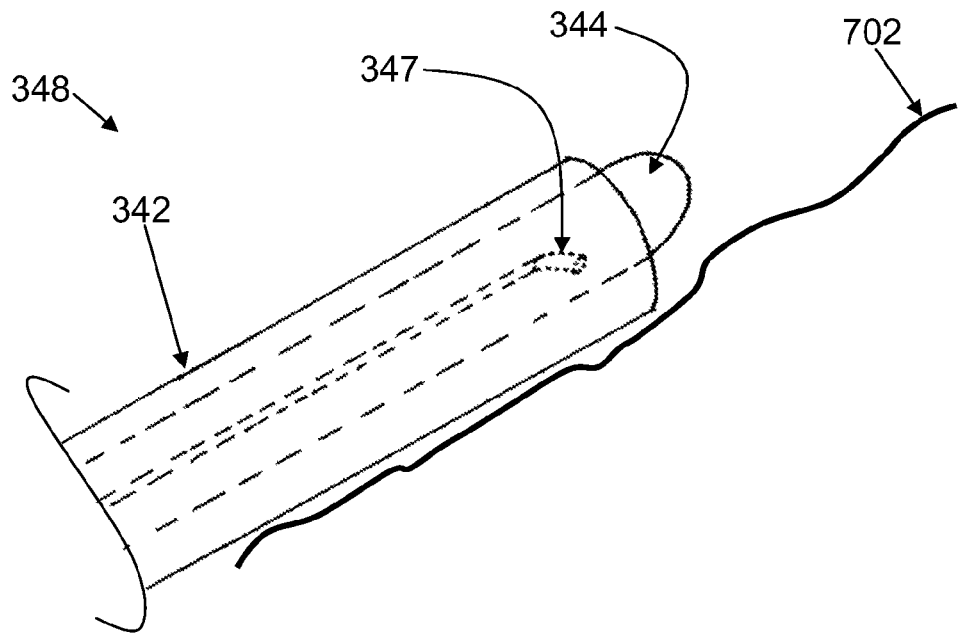
Figure 7C:
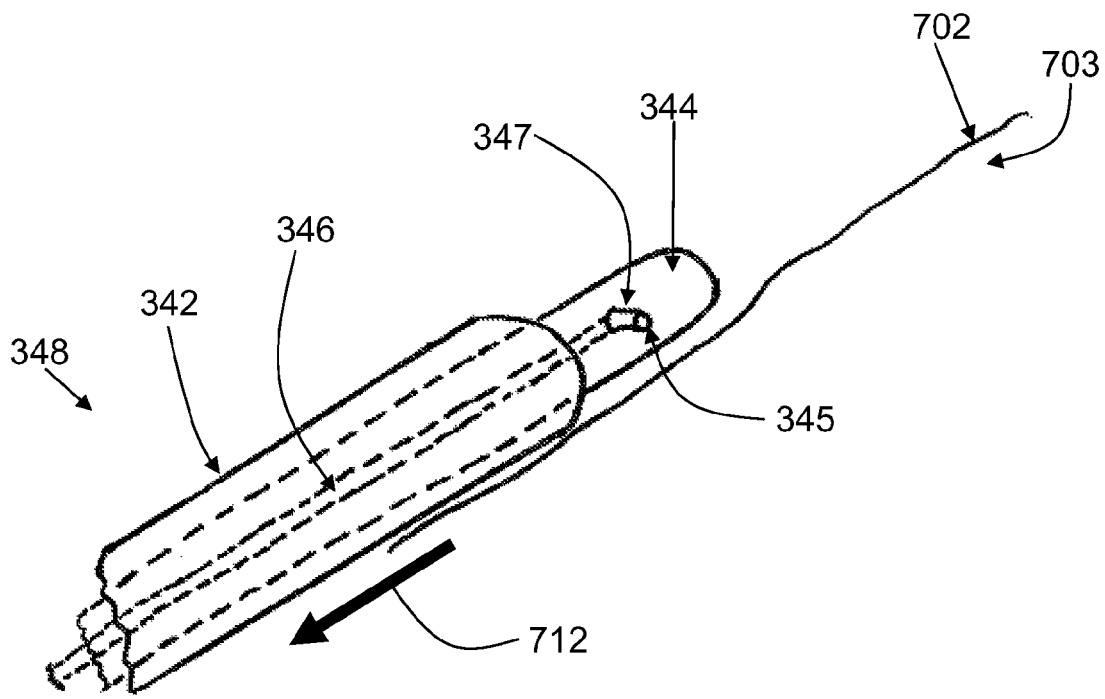
Figure 7D:
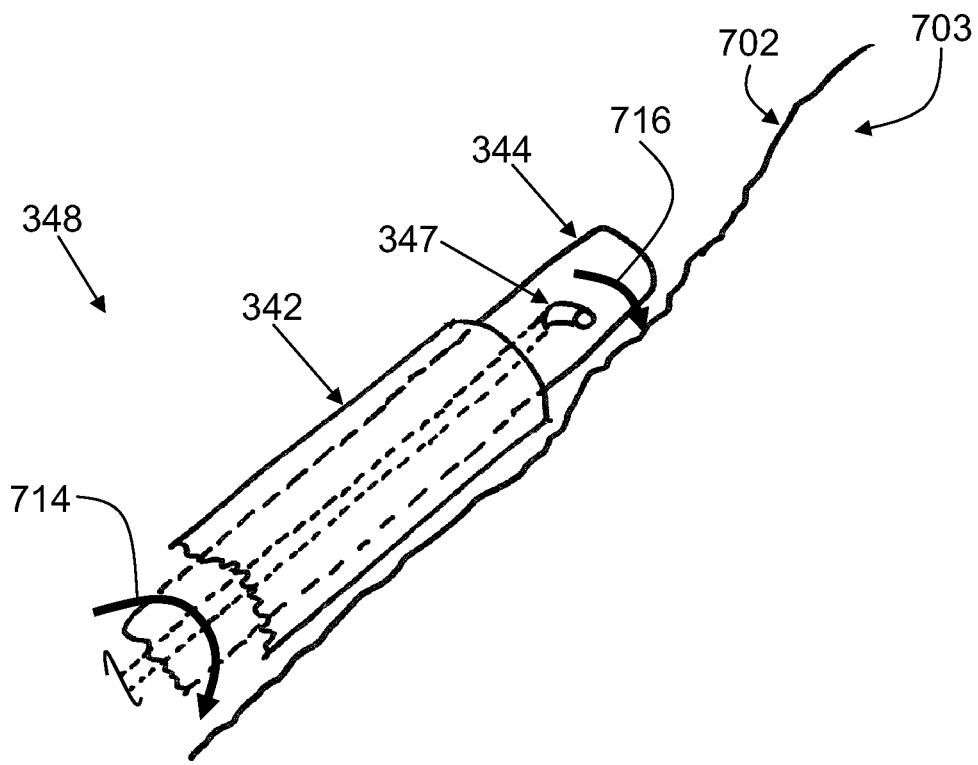
Figure 7E:
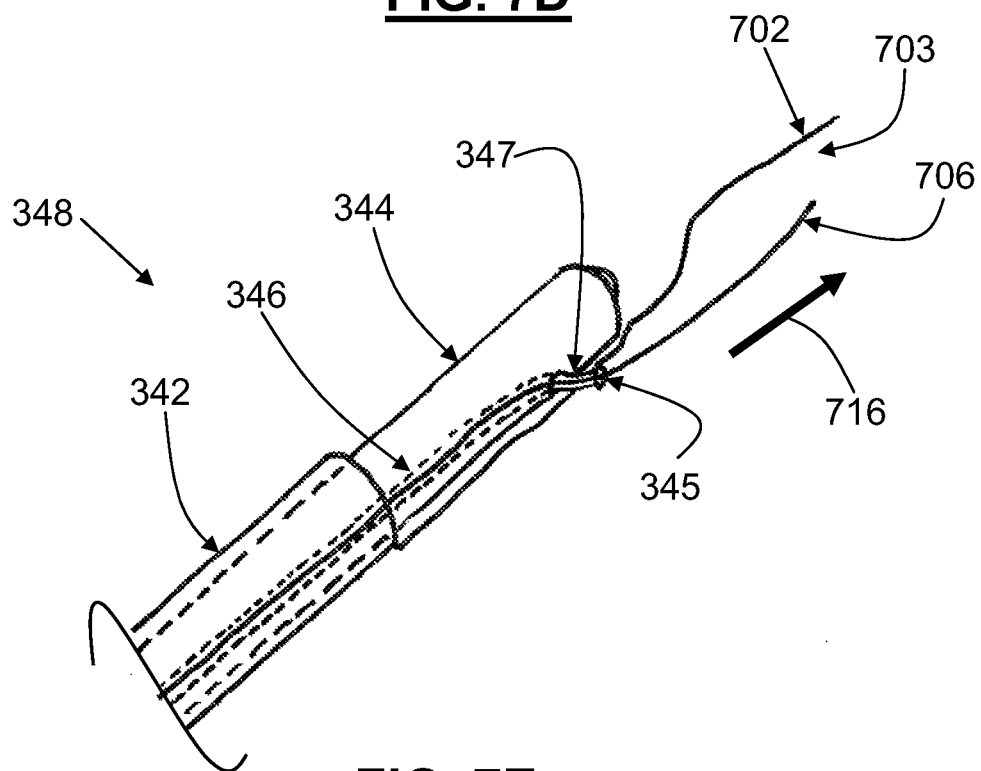

Once the distal portion of access device (348) has been advanced to the heart (700), it may be positioned such that the longitudinal axis of the device is substantially tangential to the pericardial surface. For example, FIG. 7B depicts the device (348) positioned over a portion of the pericardium (702). As seen there, the sheath (342) is positioned over the barb (347). Once it has been determined (e.g., via visualization or tactile feedback) that the device (348) is in sufficiently close proximity to the pericardium (702), the sheath (342) may be retracted in the direction of arrow (712) to expose the barb (347), as depicted in FIG. 7C, along with the barb lumen (345) which is in communication with the catheter lumen (346). Access device (348) may be rotated, twisted, or torqued in the direction of arrow (714) (for example by rotating a proximal portion of the access device (348)), as illustrated in FIG. 7D. This may rotate a distal portion of the device according to arrow (716). Rotation of the barb (347) in the direction of the arrow (716) may help the barb (347) to hook the pericardium (702), thereby engaging and puncturing the pericardium (702). The barb (347) may be rotated through any suitable angles that enable the barb to engage the pericardium (702), as shown in FIG. 7E. For example, the barb may be rotated from about 20° to about 30°, from about 30° to about 55°, from about 50° to about 90°, from about 90° to about 120°. The rotation of the barb (347) may be generally tangential to the surface of the pericardial, which may help the barb to engage with the pericardium (702) without engaging, piercing, or puncturing the surface of the heart (700). The tangential protrusion and rotation of the barb (347) may also help to regulate the depth of pericardial puncture, and may help to provide precise puncture-depth control. As described previously, the length ($L_1$) of the barb (347) may be adjusted to encourage engagement of the pericardium (702) without damaging or piercing the heart (700). While shown in FIG. 7E as completely puncturing the pericardium, the barb (347) may not puncture through the entire thickness of the pericardium. In these variations, a separate tissue-piercing device (not shown) or a guide-element may be advanced or moved relative to barb (347) to puncture the pericardium.

Once the pericardium (702) has been engaged and/or punctured by the barb (347) (which may be confirmed, e.g., through visualization, tactile feedback, and/or passing a contrast agent into the pericardial space (703) via barb lumen (345)), a guide element such as guide wire (706) may be advanced in the direction of arrow (716) through the catheter lumen (346), through the barb lumen (345), and into the pericardial space (703), as shown in FIG. 7E. In some variations, the guide wire (706) may be configured to pierce or puncture the pericardium as it passes out of barb lumen (345) and enters the pericardial space. Once the guide wire (706) has been advanced into the pericardial space (703), the device (348) may be withdrawn, with the guide wire (706) left in place to provide pericardial access for other devices, as described above.

Figure 6A:
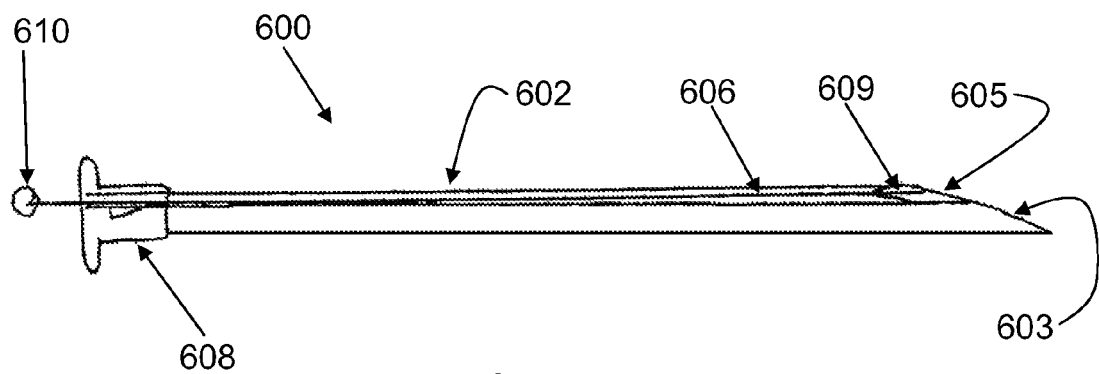
FIGS. 6A and 6B illustrate another variation of an access device that may be used with the systems and methods described herein.
Figure 6B:
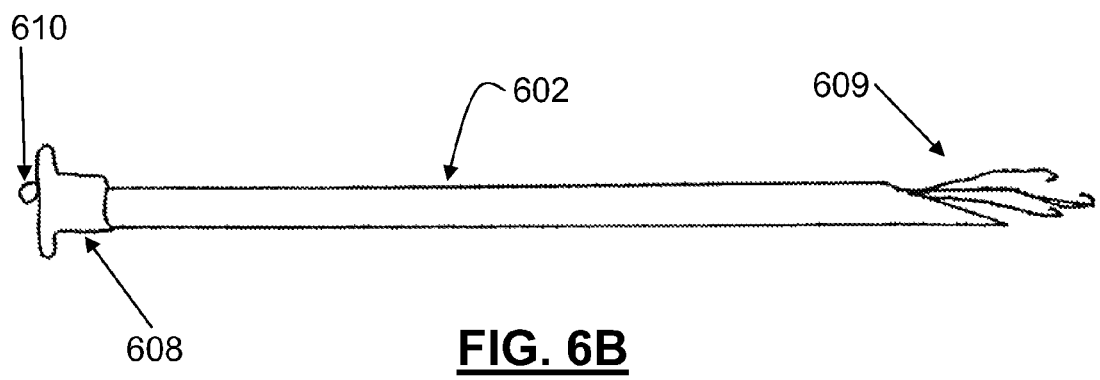

Another variation of an access device and method for accessing a pericardial space of a heart therewith is depicted in FIGS. 6A-6H. FIGS. 6A and 6B show a cross-sectional side view and a side view, respectively, of one variation of an access device (600) which may be used with a variation of method (400). As shown there, access device (600) may comprise a needle (602), tissue-engaging member (606) comprising a plurality of tissue-engaging elements (609), a guide element (not shown), a needle actuator (608) and a tissue-engaging member actuator (610). The variation of a needle shown here has a first longitudinal lumen (605) and a second longitudinal lumen (603), where both longitudinal lumens (605) and (603) terminate at an opening in the distal portion of the needle (602). While shown in FIGS. 6A-6H as comprising a needle (602), it should be appreciated that access device (600) may comprise any suitable tissue-piercing device such as those described above.

The needle actuator (608) may control the movement (e.g., rotate, advance, withdraw, etc.) and navigation of the needle (602), while the tissue-engaging member actuator (610) may control the movement, navigation, and deployment of the tissue-engaging member (606). FIG. 6A shows the tissue-engaging member (606) in an undeployed configuration, where the tissue-engaging elements (609) are collapsed within the first lumen (605). FIG. 6B shows the tissue-engaging member (606) in a deployed configuration, where the tissue-engaging elements (609) are expanded from the opening of the first lumen (605) at the distal portion of the needle (602). Tissue-engaging elements (609) may be self-expandable, as described in more detail above, but need not be. As shown there, the tissue-engaging elements (609) comprise hooks at the distal most ends to help engage the pericardium. Other variations of tissue-engaging members and tissue-engaging elements may be used with the access device (600) as suitable, for example, tissue-engaging members and elements described above and depicted in FIGS. 3A-3F may be used with this access device.

Figure 6C:
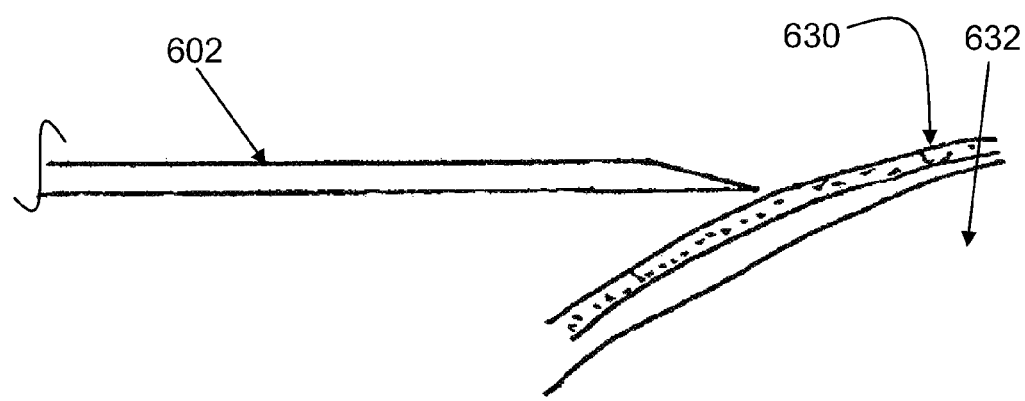
FIGS. 6C-6H depict the use of an illustrative access device to engage, manipulate, and penetrate the pericardium of a heart to access the pericardial space.
Figure 6D:
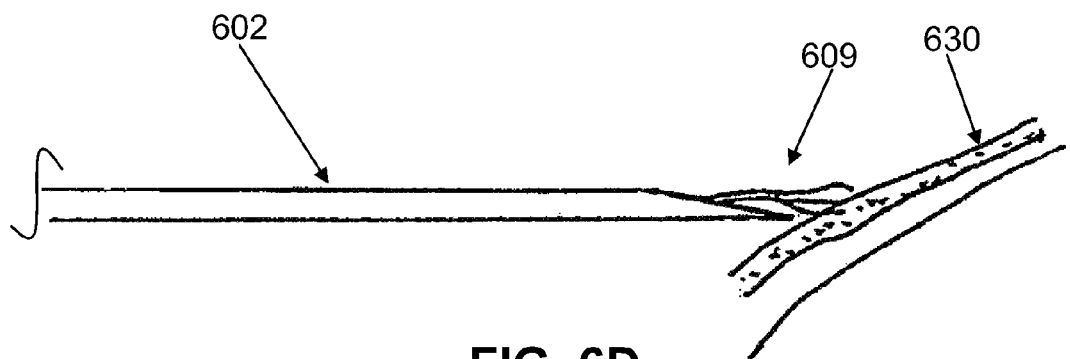
Figure 6E:
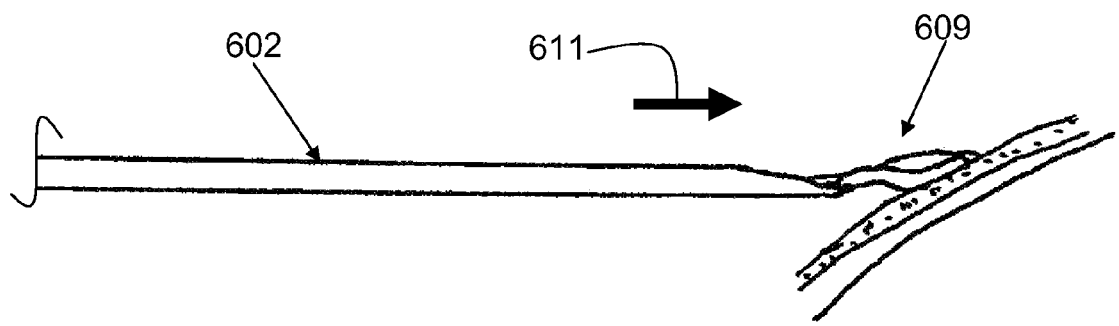
Figure 6F:
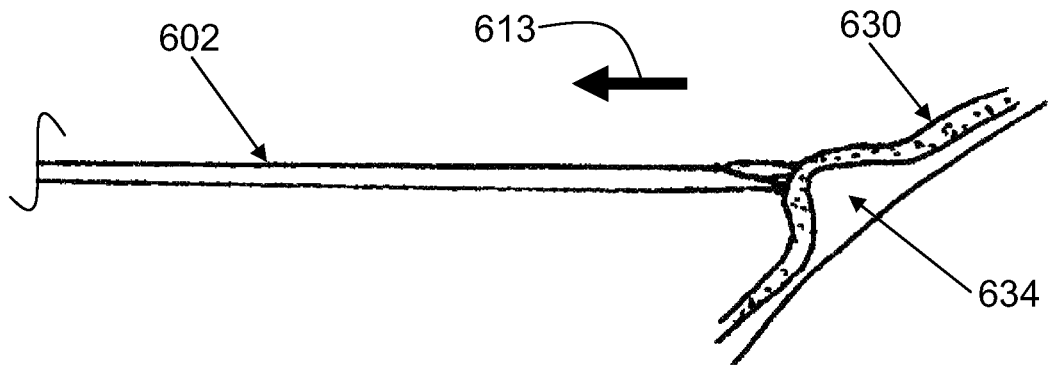
Figure 6G:
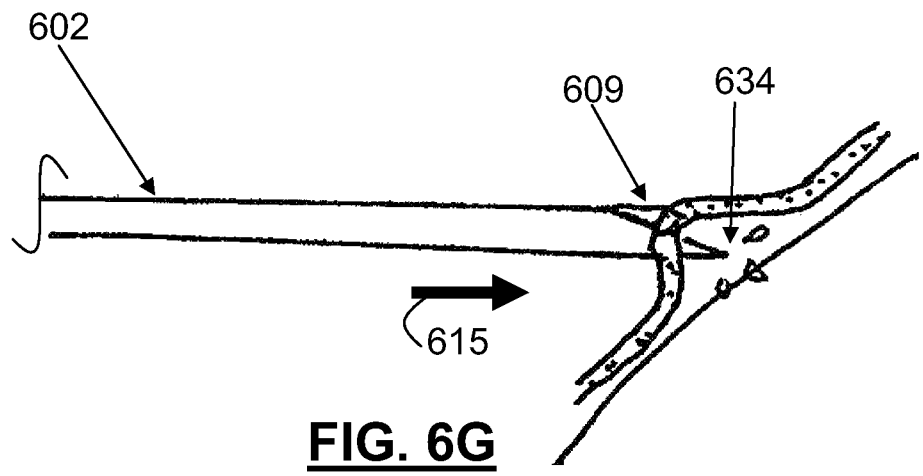
Figure 6H:
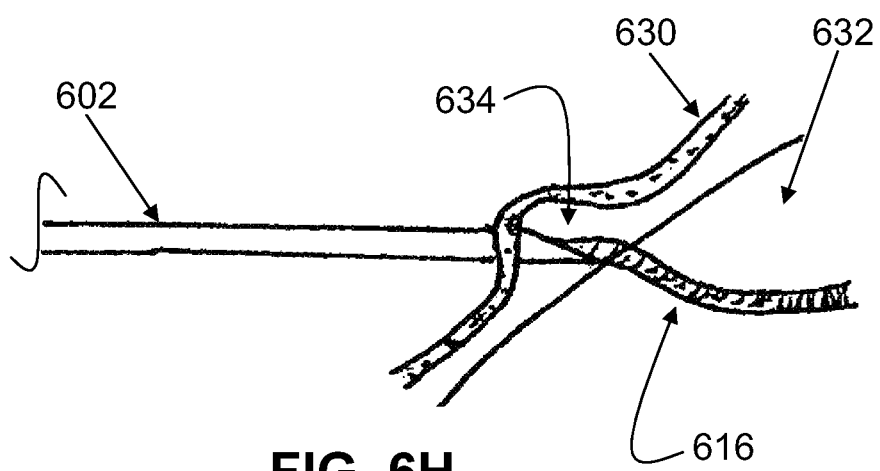

FIGS. 6C-6H depict a method by which access device may be utilized to place a guide element (616) into the pericardial space (634). As shown in FIG. 6C, the access device (600) is advanced towards the surface of the pericardium (630), where the needle (602) is positioned in close proximity to the pericardium. In some variations, the needle (602) may be positioned such that a portion of the needle (602) contacts the pericardium. In some variations, the access device (600) may comprise a sheath (not shown), such as those described above, through which the needle (602) may be advanced. The tissue-engaging member (606) may be deployed, such that the tissue-engaging elements (609) are expanded and extend outwards from the distal portion of needle (602), as shown in FIG. 6D. The tissue-engaging member actuator (610) may be used to advance the tissue-engaging elements (609) in the direction of arrow (611) to engage a portion of the pericardium (630), illustrated in FIG. 6E. After the pericardium (630) is engaged (e.g., by hooking, biting, or otherwise grabbing the pericardium (630)), the pericardium (630) may be manipulated to pull the pericardium (630) away from the surface of the heart (632), which may increase the pericardial space (634) at the intended puncture site. For example, as shown in FIG. 6F, the issue-engaging member actuator (610) may be actuated to retract the tissue-engaging elements (609) in the direction of arrow (613), e.g., away from heart (634), which may help to increase the distance between a portion of the pericardium and the surface of the heart. This may help create a locally enlarged region of pericardial space (634) at the intended puncture site. The needle actuator (608) may be used to advance the needle (602) in the direction of arrow (615) as in FIG. 6G, e.g., towards heart (632), piercing the pericardium and entering the pericardial space (which may be confirmed using any of the methods described below). In some variations, retraction of the tissue-engaging elements (609) may pull the pericardium (630) against the needle (602) to puncture the pericardium (630). In other variations, the tissue-engaging elements (609) may be retracted simultaneously with advancement of needle (602) to puncture the pericardium (630). Once the needle (602) is confirmed to have entered the pericardial space, a guide element (616), which may be housed in the second lumen (603), may be advanced out of the needle (602) into the pericardial space (634).

Figure 8A:
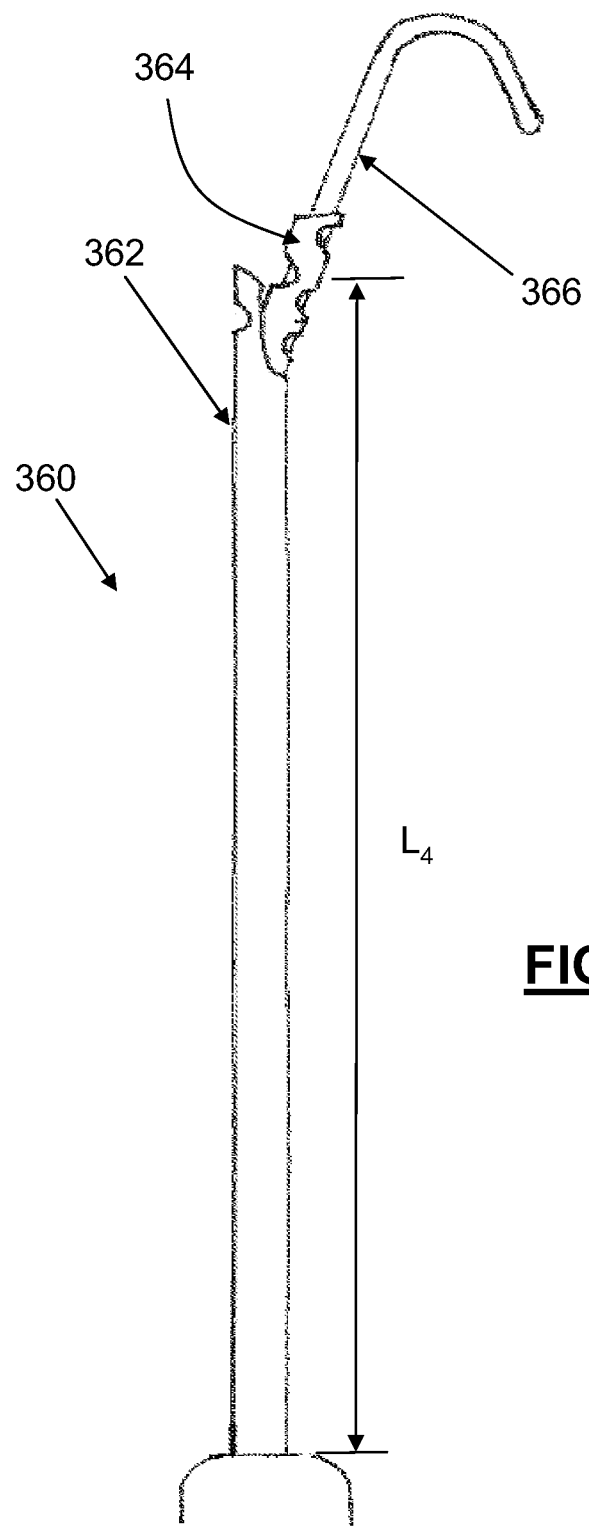
FIGS. 8A-8J depict another variation of a device and method that may be used to access the pericardial space of a heart.
Figure 8B:
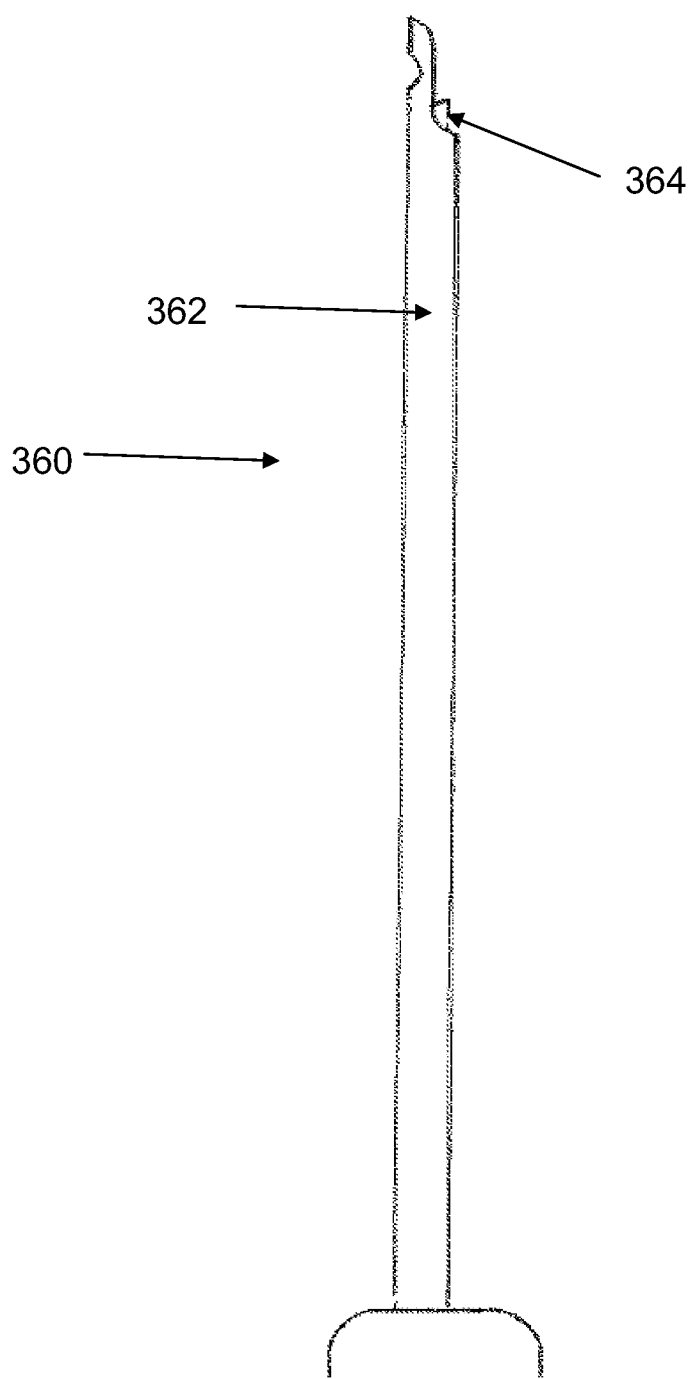
Figure 8C:
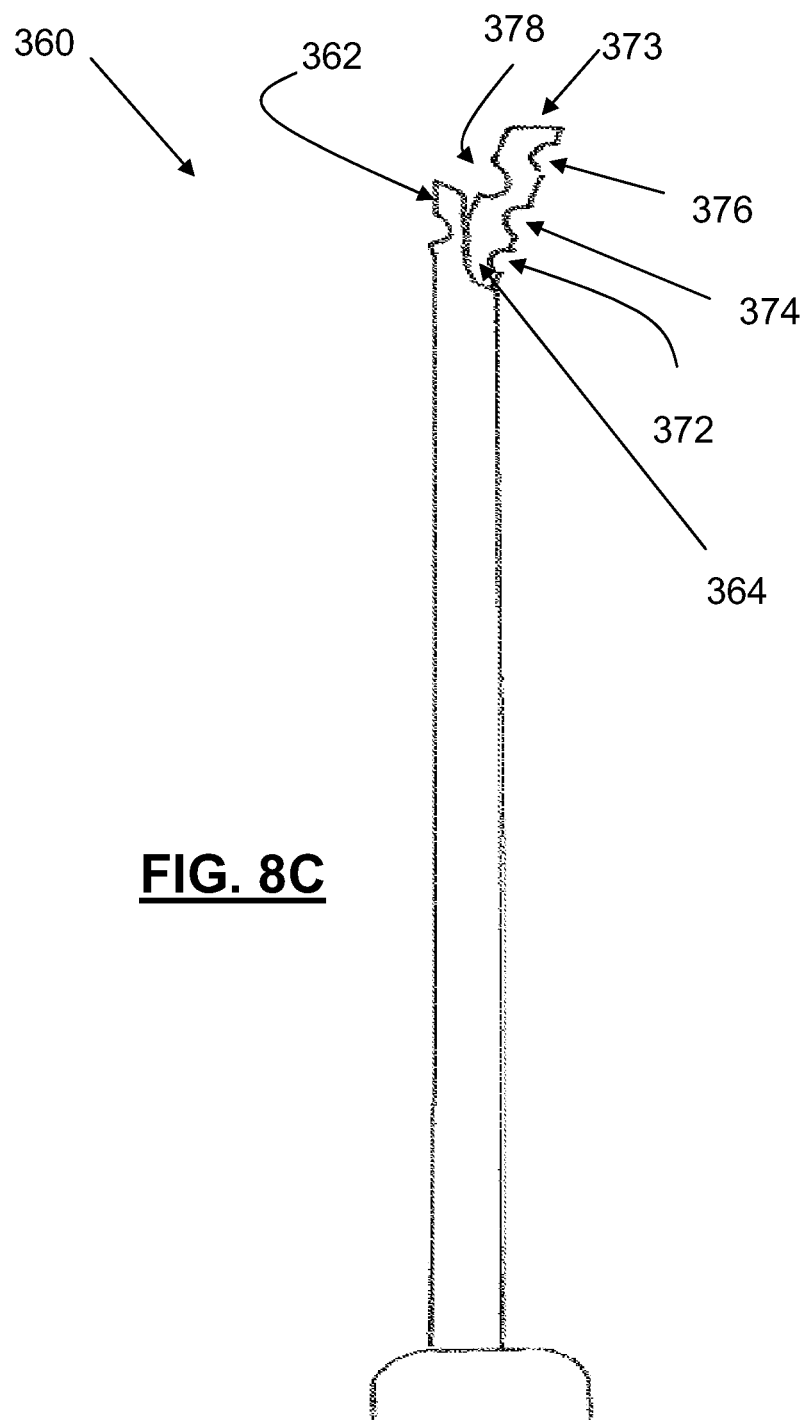
Figure 8D:
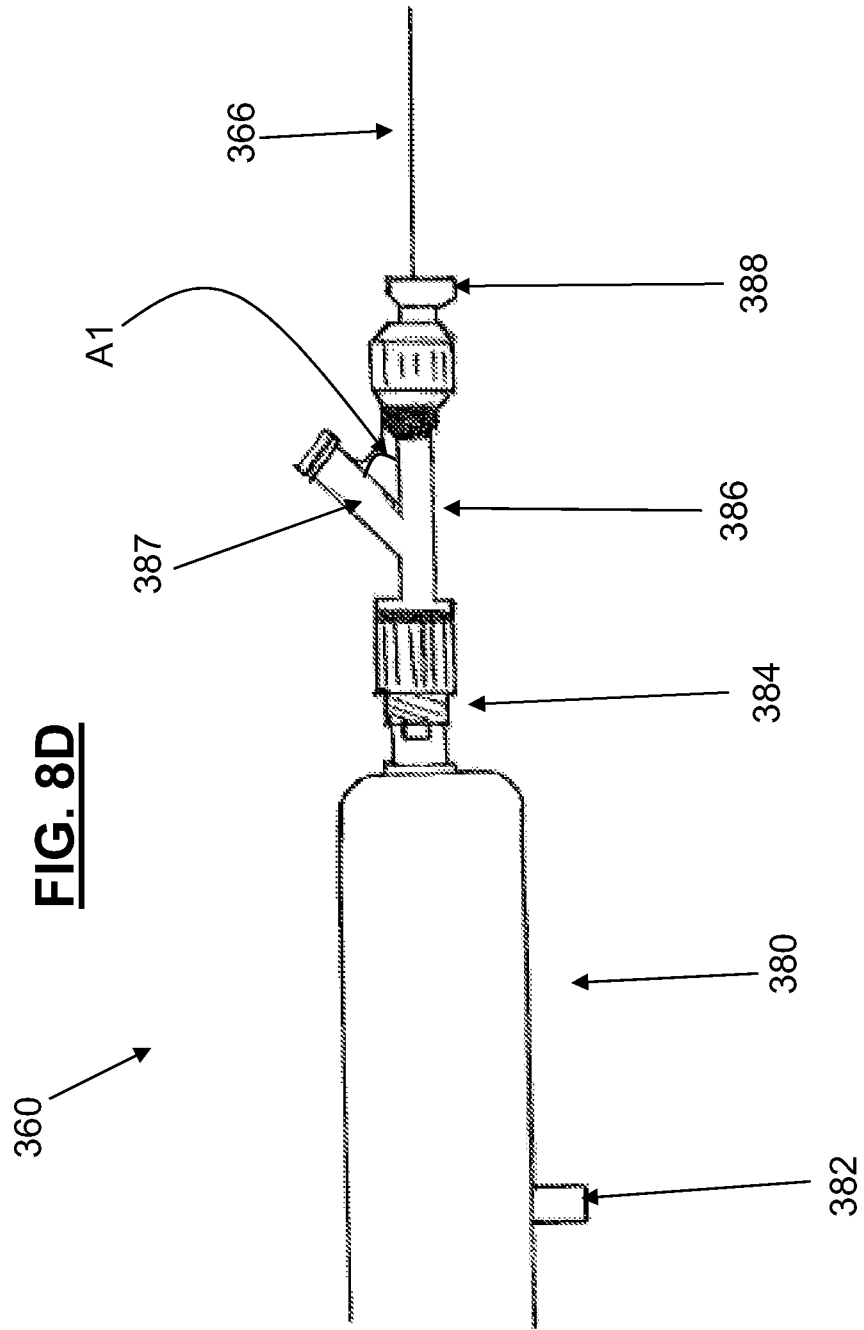
Figure 8E:
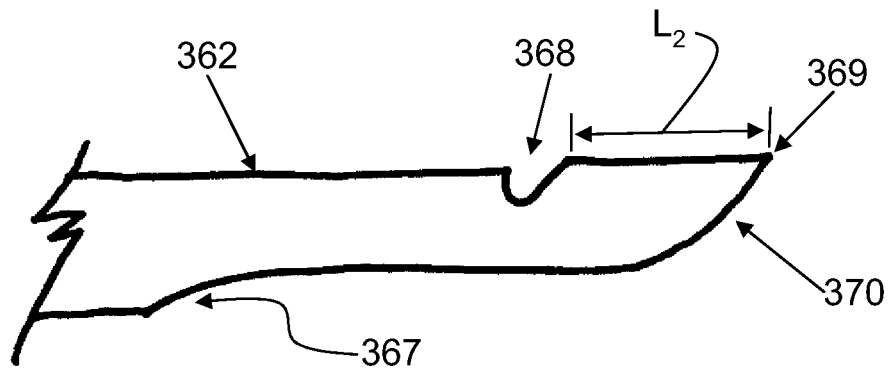

FIGS. 8A-8J depict another device and method that may be used to access the pericardial space. FIG. 8A shows one variation of the access device (360) depicted in FIG. 3H. The engagement element (362) may have a length ($L_4$) that may be determined in part by the access route selected to the heart. For example, the length ($L_4$) may be from about 100 millimeters to about 250 millimeters (e.g., about 150 millimeters to about 170 millimeters), for a subxiphoid approach to the heart via a thoracostomy, while the length ($L_4$) may be from about 50 millimeters to about 150 millimeters, (e.g., about 80 millimeters to about 150 millimeters) for an approach via a sternotomy. Also shown in FIG. 8A is the inner tubular body (364) (which may be slidably housed within the engagement element (362)) and the guide wire (366) (which may be advanced through the inner tubular body (364)). FIG. 8B depicts the device (360), where the inner tubular body (364) is largely retracted into the lumen of the engagement element (362). In some variations, the inner tubular body may be a needle, a hypotube, a tuohy needle, and the like. FIG. 8C depicts the device (360), where the inner tubular body (364) is advanced such that side apertures (372, 374, 376, 378) and lumen (373) are exposed distally from the engagement element (362). FIG. 8D depicts one variation of the proximal portion of the device (360), which comprises a handle (380) and a valve (386) connected distally to the handle (380) via a valve connector (384). The valve (386) and valve connector (384) may have a lumen configured to accommodate the guide wire (366) therethrough. The handle (380) may comprise one or more actuators as described in other handle variations, for example, a slider (382) that may be configured to advance or retract the inner tubular body (364) relative to engagement member (362). Optionally, the device (360) may also comprise a travel limiter (388) attached to the guide wire (366) which may engage with the proximal end of valve (386) to limit the advancement of guide wire (366). As seen in FIG. 8D, the valve (386) may comprise one or more ports, for example, a valve port (387) that is in fluid communication with the lumen of the engagement element (362). The valve port (387) may be slanted at an angle (A1) with respect to the valve (386), where the angle (A1) may be from about 10° to about 180°, e.g., about 30°. Various fluids may be introduced through the valve port (387) for delivery to the heart through the lumen of the engagement element (362). For example, the valve port (387) may be used to provide contrast agents, saline flush solutions, therapeutic agents, as well as gaseous fluids, such as gases for insufflation (e.g., $CO_2$, $N_2O$, He, $N_2$, etc.) through the valve port, into the engagement element, to the heart. In some variations, a guide and/or piercing element may be advanced through the valve (386) concurrently with the infusion of a fluid through the valve port (387). For example, contrast agents may be infused as a guide element is advanced, so that the distal portion of the guide element may be visualized. This may help the practitioner precisely position the guide element with respect to the heart.

Figure 8F:
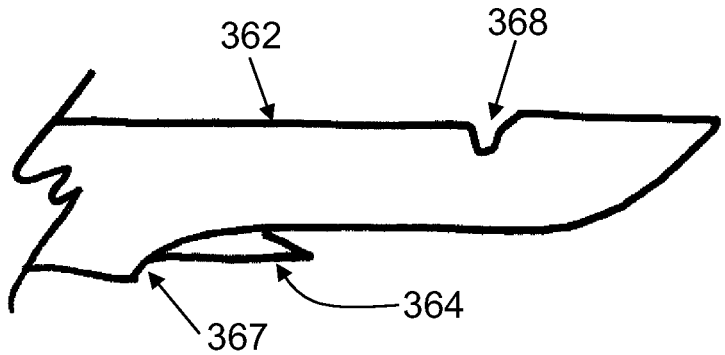
Figure 8G:
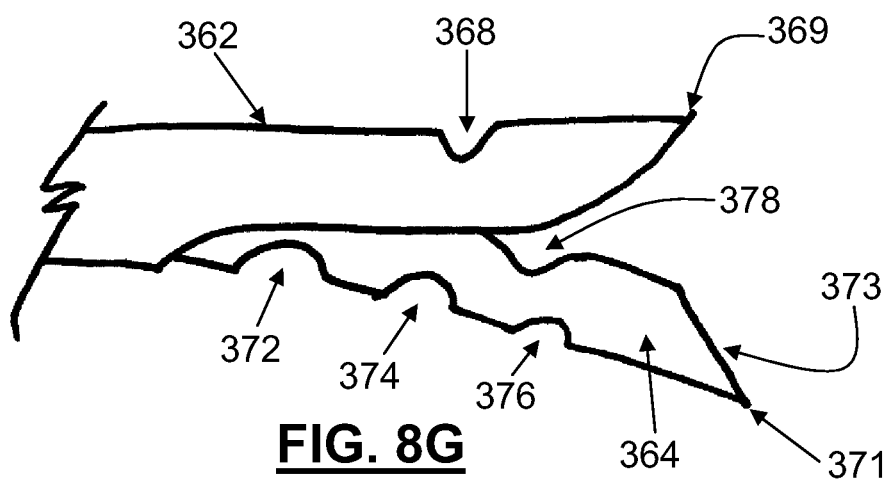
Figure 8H:
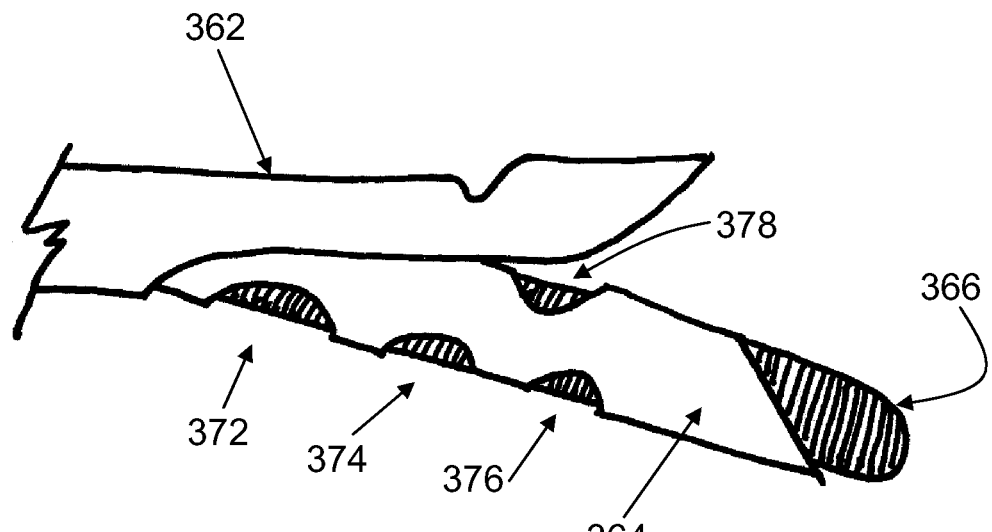
Figure 8I:
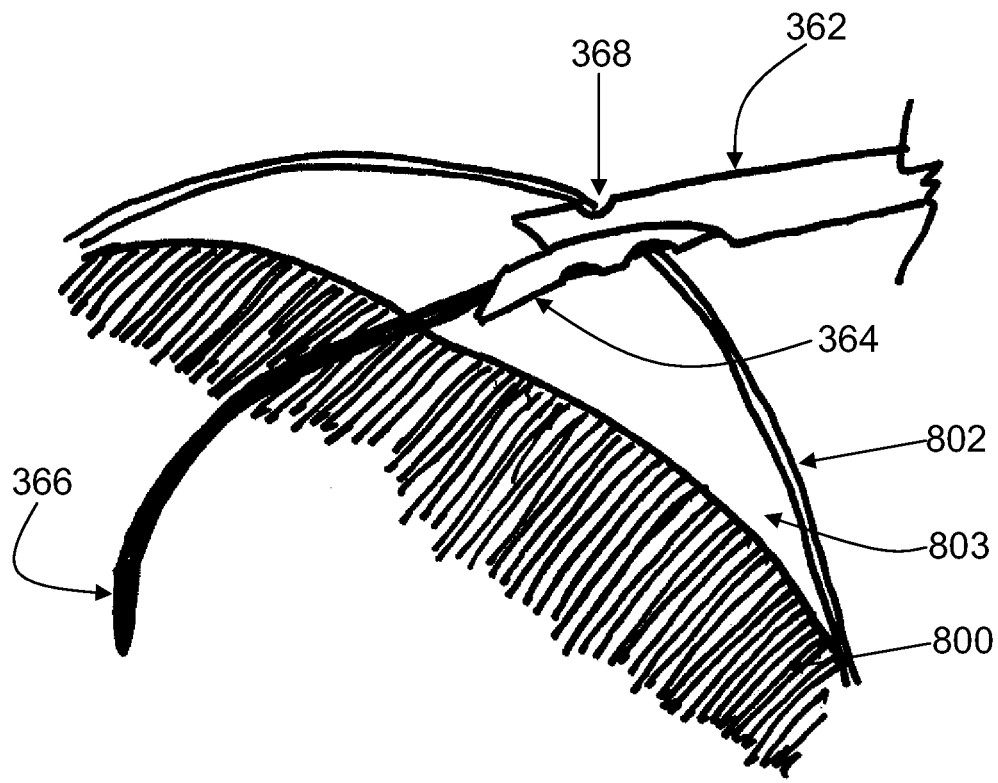
Figure 8J:
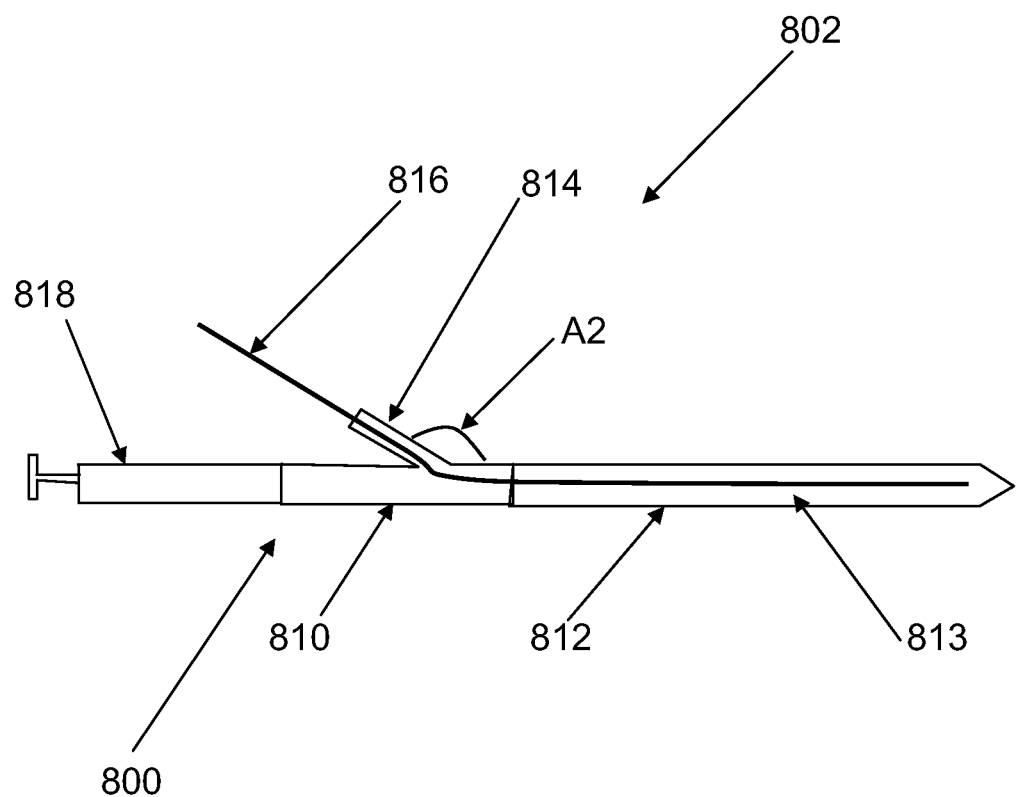

FIG. 8J shows a second variation of a handle portion (800) of an access device (802) similar to access device (360) described immediately above. As shown there, access device (802) may an engagement element (812) (such as engagement element (362) described in relation to FIGS. 8A-8I) or other tissue piercing element, a handle (800) comprising a valve (810) and valve port (800), and a guidewire (816). In some variations, the access device (800) may comprise an inner tubular member (not shown) As shown there, a syringe (818) may be connected to handle (800) via the valve (810). The syringe (818) that may retain a contrast agent, which may be introduced to a lumen of the inner tubular member and/or the engagement element (812). The valve (810) comprises a valve port (814) that may be slanted at an angle (A2) with respect to the valve (810), where the angle (A2) may be from about 10° to about 180°, e.g., about 150°. The distal portion of the valve (810) may be coupled to the engagement element (812), which may be used to engage or otherwise access the pericardium as described herein. A guidewire (816) may be advanced via the side port (814) and into the lumen of the engagement element (812) and/or a lumen of an inner tubular member. During use, the engagement element (812) may pierce and create an access port through the pericardium. Once the engagement element (812) has advanced through the pericardium, e.g., into the pericardial space, the guide wire (816) may be introduced or otherwise advanced through the valve port (814), through the lumen (813), and advanced into the pericardial space. Simultaneously or sequentially, contrast agents or stains in the syringe (818) may be injected to allow a practitioner to image the pericardial space. The valve port (814) may help to reduce the number of steps needed to image the pericardial space and advance the guide wire. For example, the valve (810) may help to reduce the amount of time spent attaching the contrast agent syringe to image the pericardial space, and detaching the syringe to advance the guide wire. Reducing the number of steps, and attachment detachment iterations may also help to reduce the risk of unintentionally puncturing heart tissue.

Returning to FIGS. 8A-8J, after the access device (360) has been introduced into the chest cavity through any of the access routes previously described, the device may be advanced towards the heart in the configuration shown in FIG. 8E, where the inner tubular body (364) with retracted within the engagement element (362). Once the engagement element (362) has been advanced to, and positioned along the pericardium, it may be actuated, advanced, or otherwise manipulated to puncture the pericardium with the distal tip (369), and advanced so that the pericardium is engaged in the groove (368). The depth of penetration of the engagement element may be determined in part by length ($L_2$), e.g., the puncture depth may be limited to about length ($L_2$). The rounded edge (370) may help to prevent puncturing the heart while the distal tip (369) punctures the pericardium. In some variations, after the engagement element (362) has punctured and engaged the pericardium (which may be confirmed by any suitable method described below), the engaging element (362) may optionally be lifted, moved, or otherwise manipulated to lift the pericardium away from the surface of the heart. The access device (360) may be actuated such inner tubular body (364) may be advanced through the aperture (367), as shown in FIGS. 8F and 8G.

As shown there, the inner tubular body (364) may be initially be constrained by engagement element (362) such that inner tubular body (364) may be advanced in a direction parallel to the longitudinal axis of the engagement element (362), as shown in FIG. 8F. As inner tubular body (364) exits engagement element (362) through aperture (367), the inner tubular body (364) may angle away from the engagement element (362), as shown in FIG. 8G. It should be appreciated the inner tubular body (364) may move through aperture in any suitable manner (e.g., parallel to the longitudinal axis of the engagement element (362) or at an angle from the engagement element). As the inner tubular body (364) is advanced, the sharpened tip (371) may also puncture the pericardium and enter the pericaridail space. In some variations, advancement of the tubular body (364) may place the side apertures (372, 374, 376, 378) into the pericardial space. When the apertures are in the pericardial space, various fluids that may be introduced to the pericardial via the valve port (387), for example, contrast agents, therapeutic agents, flush solutions, insufflation liquids and/or gases, and the like. Additionally, while distal end of the inner tubular body (364) is placed in the pericardial space, the guide wire (366) may be advanced, as shown in FIGS. 8H and 8I, through the inner tubular body (364) into the pericardial space. FIG. 8I depicts an example of how the groove (368) may be used to engage the pericardium (802) and enlarge a portion of the pericardial space by increasing the distance between the pericardium (802) and the heart (800). Once a region of the pericardial space has been enlarged, the inner tubular body (364) may be advanced into the pericardial space (803). Additionally or alternatively, in some variations the pericardium may be manipulated after by engagement element (362) and inner tubular body (364) after advancement of the inner tubular body (364). The guide wire (366) may be placed in the pericardial space (803), after which the inner tubular body, engagement member, and other components may be withdrawn, as appropriate. In variations where inner tubular member (364) is advanced out of engagement element (362) at an angle relative to the engagement element (362), the guidewire may also be introduced into the pericardial space at an angle relative to the engagement element (362).

While certain variations of methods and mechanisms of engaging a portion of the pericardium have been described above, additional and/or alternative methods and mechanisms of engaging pericardial tissue may be used as well. For example, pericardial tissue may be mechanically engaged, where a portion of the pericardium may be pinched, cinched, clasped, grasped, pulled, hooked, grappled, and the like. Devices that may mechanically engage a portion of pericardial tissue for manipulation include hemostats, pinchers, clamps, drawstring mechanisms, pins, hooks, and clasps. Pericardial tissue may also be engaged by using suction or vacuum devices, which may act to pull the pericardium away from the heart to enlarge a portion of the pericardial space. Alternatively or additionally, the pericardium may be engaged by various adhesive forces, for example, molecular adhesive forces, such as hydrophobic or hydrophilic interactions. Devices that utilize magnetic forces may also be used to engage the pericardium by magnetically clamping a portion of the pericardium and the pulling on the pericardium to enlarge a portion of the pericardial space.

Manipulation of the pericardium once it has been engaged may comprise any number and combination of maneuvers that may increase the distance between a portion of the pericardium and the heart, thus locally enlarging a portion of the pericardial space. For example, the pericardium may be rotated, twisted, pulled, pushed, pierced, punctured, speared, and or insufflated with a gaseous or liquid fluid. The pericardium may also be chemically treated, which may create a puncture in the pericardium. For instance, an access device may controllably introduce enzymes to thin out a surface of the pericardium to create an access pathway. Chemical agents that may be used to manipulate the pericardium include lysosomal enzymes, acid phosphatase, aryl sulfatase, glucosaminidase, trypsin, and/or any other suitable enzyme digest. The pericardium may also be electrically manipulated, as previously described, by applying current via conductive tissue-engaging members or electrodes. In some variations, focally applying a current (between 1 pA and 200 mA) may breakdown and/or thin out regions of the pericardium. Other methods of creating a puncture or incision in the pericardium may include electrocautery, chemical cautery, cryocautery, and laser cautery.

As mentioned above, the methods described here may comprise insufflating the pericardial space with a gaseous or liquid fluid to move the pericardium away from the heart. Insufflation of the pericardial space may occur at any suitable step of the method. For example, in some variations, the pericardial space may be insufflated prior to engaging the pericardium with the access device. In other variations, the pericardial space may be insufflated after engaging the pericardium with one or more tissue-engaging members, but before piercing the pericardium with a tissue-piercing member. In still other variations, the pericardial space may be insufflated after a tissue-piercing member has punctured, pierced, or otherwise penetrated the pericardium.

When the pericardial space is insufflated, it may be insufflated in any suitable manner. In some variations, one or more portions of the access device may insufflate the pericardial space. In some of these variations, a tissue-engaging member may be used to insufflate the pericardial space. For example, in the variation of access device (348) described above in relation to FIG. 3G and FIGS. 7A-7E, the pericardial space may be insufflated via lumen (345) of barb (347) after the barb has engaged and punctured the pericardium. In others of these variations, a tissue-piercing member may be used to insufflate the pericardial space. For example, in the variation of access device (500) described above in relation to FIGS. 5A-5J, tissue-piercing member (502) may be used to insufflate the pericardial space (e.g., via first lumen (503) and/or second lumen (505) of the tissue-piercing member (502)) after the tissue-piercing member has pierced or penetrated the pericardium.

In still other variations, one or more separate devices may be used to insufflate the pericardium. In some of these variations, a needle or other member may be advanced externally from the heart, and may at least partially pass through the pericardium to insufflate the pericardial space. In some of these variations, the insufflating member may be advanced in a subxyphoid approach. In others of these variations, the insufflating member may be advanced in a transverse sinus approach. In other variations, the pericardial space may also be insufflated from an intravascular approach. For example, a balloon may be intravascularly advanced to a left atrial appendage (or any suitable portion of the heart), and expanded to occlude the left atrial appendage. An intravascular-piercing member with a lumen therethrough may be advanced through the balloon. The lumen may be connected to a gaseous or liquid fluid source. The intravascular-piercing member may then exit the left atrial appendage and enter the pericardial space. Once entry into the pericardial space from the left atrial appendage has been confirmed, gas and/or liquid may be pumped into the pericardial space until a desired distance between the pericardium and the epicardial surface of the heart has been attained. In some variations, the puncture created in the pericardium by the external piercing member and the puncture created in the left atrial appendage wall by the intravascular-piercing member may create an access port or entry point into the heart, where access is provided between the interior and exterior of the heart for the delivery of devices and therapies. Applications where this may be utilized include ablation procedures for treatment of atrial fibrillation on the endocardial and epicardial surfaces, mitral valve repair or replacement procedures, delivering devices for structural heart repair and/or CHF, ASD and PFO closure, left atrial appendage closure or combinations of any of the above.

When the pericardial space is insufflated, the amount of insufflation may be determined by, for example, measuring pressure and/or volume changes in the pericardium, or by imaging methods. In some variations, the quantity of fluid that may be introduced into the pericardial space is pre-programmed or pre-determined. When the desired distance between the pericardium and the epicardial surface of the heart has been achieved, insufflation of the pericardial space may be stopped. It should also be appreciated that the devices that may be used to insufflate the pericardium may also be used to aspirate one or more portions of the pericardium.

As mentioned above, in some variation it may be desirable to confirm entry of the piercing member into the pericardial space (410) prior to advancing a guide element therethrough. Some piercing members may possess imaging markers (e.g., echogenic markers, radiopaque markers, etc.) that allow the movement of the piercing member to be monitored by a variety of suitable imaging modalities, e.g., fluoroscopy, ultrasound, X-ray, etc.

In some variations, electrically conductive piercing members may be monitored using current and/or voltage measurements to detect a change in impedance or conductivity when the piercing member enters the pericardial space. For example, a voltage may be applied between two tissue-engaging members, and the resultant current through the medium (e.g., the pericardium, the pericardial fluid, etc.) may be measured by another tissue-engaging member. The applied voltage may be increased or decreased step-wise on across tissue-engaging members (e.g., in 20 pA), or may be pulsed, while the current is measured on the tissue-piercing member. The resultant I-V curves may indicate the location of the tissue-piercing member, for example, the I-V curves measured when the tissue-piercing member is within the pericardial sac may be different from the I-V curves measured when it is part of the way through the pericardium, etc. Since different media and tissues (e.g., air, liquid, pericardial tissue, fatty tissue, cardiac tissue, etc.) have different electrical properties (e.g., conductive, resistive, etc.), various electrical parameters other than the ones described above may be measured to determine (or at least approximate) the location of the tissue-piercing member with respect to the pericardium and the heart.

Entry of a tissue-piercing member into the pericardial space from outside the pericardial space may also be confirmed by using piercing members that are configured to differentiate between a gaseous environment (e.g., outside of the pericardial space) and a liquid environment (e.g., inside the pericardial space). For example, piercing member(s) may have a port that allows liquid fluid to flow through to a detector, e.g., liquid sensor. The detector may indicate to the practitioner that the piercing member(s) are in a liquid environment, i.e., that entry to the pericardial space has been attained. In some variations, the pericardial space may be insufflated with gas or fluid prior to advancing a tissue-piercing member with a gas and/or liquid sensor.

Another way in which entry of a tissue-piercing member into a pericardial space may be confirmed is by monitoring changes in pressure. Tissue-piercing member(s) may be associated with a pressure sensor. Examples of pressure sensors that may be used include piezoresistive strain gages, capacitive pressure sensors, electromagnetic pressure sensors, piezoelectric pressure sensors, resonant pressure sensors, and any other suitable pressure sensors. There may be a change in pressure as the piercing member enters the pericardial space, and this change in pressure may indicate to the practitioner that the tissue-piercing member is within the pericardial space. The pressure experienced by the tissue-piercing member may be constantly monitored to detect for an abrupt change in pressure that may be expected once the tissue-piercing member pierces and enters the pericardium.

Although the foregoing invention has, for the purpose of clarity and understanding been described in some detail by way of illustration and example, it will be apparent that certain changes and modifications may be practiced, and are intended to fall within the scope of the appended claims.

We claim:

1. A method for accessing a pericardial space of a heart comprising:
   inserting a device into a chest cavity, wherein the device comprises a tissue-piercing member having a longitudinal axis, a tissue-engaging member, and a first guide element;
   deploying the tissue-engaging member through a lumen of the tissue-piercing member from a low-profile undeployed configuration to an expanded deployed configuration;

engaging a portion of an external surface of a pericardium with the expanded tissue-engaging member;

manipulating the engaged portion of the pericardium to increase the distance between the engaged portion of the pericardium and the heart;

advancing the tissue-piercing member through the pericardium into the pericardial space; and advancing at least a portion of the guide element into the pericardial space through the lumen of the tissue-piercing member.

2. The method of claim 1, wherein manipulating the engaged portion of the pericardium comprises rotating the tissue-piercing member around its longitudinal access.

3. The method of claim 1, wherein the device further comprises a sheath having a longitudinal axis, and wherein manipulating the engaged portion of the pericardium comprises rotating the sheath around its longitudinal axis.

4. A method for accessing a pericardial space of a heart comprising:

advancing a device into a chest cavity, wherein the device comprises an engagement element, an inner tubular body, and a guidewire, wherein the engagement element comprises a sharpened distal tip, a penetration limiter for engaging a pericardium, a first lumen therethrough, and a distal aperture, wherein the inner tubular body comprises a first lumen therethrough and is slidably disposed in the first lumen of the engagement element, and wherein the guidewire is advanceable through the first lumen of the inner tubular body;

puncturing the pericardium with the sharpened distal tip of the engagement element and advancing the sharpened distal tip into the pericardial space;

engaging a portion of the pericardium with the penetration limiter;

advancing the inner tubular body into the pericardial space; and advancing the guidewire through the inner tubular body and into the pericardial space.

5. The method of claim 4 further comprising manipulating the engaged portion of the pericardium.

6. The method of claim 4 further comprising introducing one or more gases or fluids into the pericardial space through the first lumen of the inner tubular member.

* * * * *